US007482429B2

(12) United States Patent  (10) Patent No.: US 7,482,429 B2
Albericio et al.  (45) Date of Patent: Jan. 27, 2009

(54) KAHALALIDE F AND RELATED COMPOUNDS

(75) Inventors: Fernando Albericio, Barcelona (ES); Ernest Giralt, Barcelona (ES); Jose Carlos Jimenez, Barcelona (ES); Angel Lopez, Barcelona (ES); Ignacio Manzanares, Madrid (ES); Ignacio Rodrigues, Madrid (ES); Miriam Royo, Barcelona (ES)

(73) Assignee: Pharma Mar, S.A., Madrid (ES)

( * ) Notice: Subject to any disclaimer, the term of this patent is extended or adjusted under 35 U.S.C. 154(b) by 0 days.

(21) Appl. No.: 10/182,881

(22) PCT Filed: Feb. 9, 2001

(86) PCT No.: PCT/GB01/00576

§ 371 (c)(1), (2), (4) Date: Jun. 3, 2003

(87) PCT Pub. No.: WO01/58934

PCT Pub. Date: Aug. 16, 2001

(65) Prior Publication Data

US 2004/0214755 A1    Oct. 28, 2004

(30) Foreign Application Priority Data

Feb. 9, 2000 (GB) .................................. 0002952.0

(51) Int. Cl.
A61K 38/00 (2006.01)
A61K 38/03 (2006.01)

(52) U.S. Cl. .................. 530/327; 530/326; 530/328; 530/329; 530/333; 514/14; 514/13; 514/15; 514/16; 514/17

(58) Field of Classification Search .................. 530/350
See application file for complete search history.

(56) References Cited

U.S. PATENT DOCUMENTS

| 4,670,261 | A |   | 6/1987  | Samejima et al. |
| 4,959,175 | A | * | 9/1990  | Yatzidis ...................... 252/364 |
| 5,705,511 | A |   | 1/1998  | Hudkins et al. |
| 5,849,704 | A |   | 12/1998 | Sorensen et al. |
| 5,932,189 | A | * | 8/1999  | Dean et al. ................. 424/1.69 |
| 6,011,010 | A |   | 1/2000  | Scheuer et al. .............. 514/11 |
| RE39,496  | E | * | 2/2007  | Scheuer et al. .............. 514/9 |
| 2003/0157685 | A1 | * | 8/2003 | Zervos ...................... 435/226 |
| 2004/0052764 | A1 | * | 3/2004 | Hildinger et al. ............ 424/93.2 |
| 2004/0067895 | A1 |   | 4/2004 | Faircloth |
| 2005/0054555 | A1 |   | 3/2005 | Jimeno |
| 2006/0234920 | A1 |   | 10/2006 | Faircloth |
| 2007/0032412 | A1 |   | 2/2007 | Izquierdo Delso |

FOREIGN PATENT DOCUMENTS

| EP | 0 610 078 A1 | 8/1994 |
| EP | 0 838 221 A1 | 4/1998 |
| WO | WO 99/42125 | 8/1999 |
| WO | WO 02/36145 | 5/2002 |

OTHER PUBLICATIONS

Isabelle Bonnard, Ignacio Manzanares, and Kenneth L. Rinehart, Stereochemistry of Kahalalide F, J. Nat. Prod, vol. 66, 2003, pp. 1466-1470.*
McKie (R McKie. Cancer Research Set Back a Decade. The Observer (Jun. 10, 2001) pp. 1-4 (HTML text).*
Freshney, Culture of Animal Cells, A Manual of Basic Technique, Alan R. Liss, Inc., 1983, New York, pp. 3-4.*
Zips (Daniel, Zips, et al., New Anticancer Agents: in Vitro and In Vivo Evaluation, In Vivo (2005) 19: 17.*
GB Dermer. Another Anniversary for the War on Cancer. Bio/Technology Mar. 12, 1994 pp. 1-2.*
T Gura. Systems for Identifying New Drugs are Often Faulty. Science (1997) 278 (Nov. 7) 1041-1042.*
(C Gorman, et al. The Hype and the Hope. Time (1998) 151 (19) pp. 40-44. Included HTML copy referenced pp. 1-9.*
"cancer" [internet document] accessed Sep. 16, 2005 /www.medterms.com>, last reviewed Sep. 18, 2004, 1 page.*
R. McKie, Cancer Researc Set Back a Decade, The Observer, Jun. 10, 2001, pp. 1-4 (HTML text).*
Daniel Zips, et al., New Anticancer Agents: In Vitro and In Vivo Evaluation, In Vivo, 2005, 19:1-7.*
GB Dermer, Another Anniversary for the War on Cancer, Bio/Technology, Mar. 12, 1994, pp. 1-2.*
T. Gura, Systems for Identifying New Drugs are Oten Faulty, Science, Nov. 7, 1997, 278, pp. 1041-1042.*
C. Gorman, et al. The Hype and the Hope, Time, 1998, 151(19), pp. 40-44, included HTML copy referenced pp. 1-9.*
"Cancer" [internet document] accessed Sep. 16, 2005, www.medterms.com, last reviewed Sep. 18,2004, 1 pages.*
of Hamann, et al. Kahalalide: Bioactive peptides from a marine Mollusk Elysia rufescens and its Algal diet Bryopsis sp., J. Org. Chem., 1996, vol. 61, pp. 6594-6600.*
El Sayed, Khalid A. et al., "The Marine Environment: A Resource for Prototype Antimalarial Agents", *Journal of Natural Toxins*, vol. 5, No. 2, pp. 261-285 (1996).
Garcia-Rocha, Mar et al., "The antitumoral compound Kahalalide F acts on cell lysosomes", *Cancer Letters*, vol. 99, No. 1, pp. 43-50 (1996).

(Continued)

*Primary Examiner*—Cecilia Tsang
*Assistant Examiner*—Jennifer I Harle
(74) *Attorney, Agent, or Firm*—King & Spalding, LLP; Kenneth H. Sonnenfeld; Michael A. Willis

(57) ABSTRACT

A process is provided for preparing kahalalide F and which leads to other kahalalide mimic compounds having useful biological activity.

49 Claims, No Drawings

OTHER PUBLICATIONS

Goetz, Gilles et al., "The Absolute Stereochemistry of Kahalalide F", *Tetrahedron*, vol. 55, pp. 7739-7746 (1999).

Goetz, G. et al., "Two Acyclic Kahalalides from the Sacoglossan Mollusk Elysia rufescens", *Journal of Natural Products*, vol. 60, No. 6, pp. 562-567 (1997).

Hamann, Mark T. et al., "Kahalalide F: A Bioactive Depsipeptide from the Sacoglossan Mollusk Elysia refuscens and the Green Alga Bryopsis sp.[1]", *Journal of the American Chemical Society*, vol. 115, No. 13, pp. 5825-5826 (1993).

Hamann, Mark T. et al., "Kahalalides: Bioactive Peptides from a Marine Mollusk Elysia refuscens and Its Algal Diet Bryopsis sp[1]", *The Journal of Organic Chemistry*, vol. 61, No. 19, pp. 6594-6600 (1996).

Hamann, Mark T. et al., "Kahalalides: Bioactive Peptides from a Marine Mollusk Elysia refuscens and Its Algal Diet Bryopsis sp.[1]", *The Journal of Organic Chemistry*, vol. 63, No. 14, pp. 4856 (1998).

Horgen, F. David et al., "A New Depsipeptide from the Sacoglossan Mollusk Elysia ornate and the Green Alga Bryopsis Species[1]", *Journal of Natural Products*, vol. 63, No. 1, pp. 152-154 (2000).

Kan, Yukiko et al., "Kahalalide K: A New Cyclic Depsipeptide from the Hawaiian Green Alga Bryopsis Species", *Journal of Natural Products*, vol. 62, No. 8, pp. 1169-1172 (1999).

Lopez-Macia, Angel et al., "Kahalalide B. Synthesis of a natural cyclodepsipeptide", *Tetrahedron Letters*, vol. 41, pp. 9765-9769 (2000).

Nuijen, B. et al., "Development of a Lyophilized Parenteral Pharmaceutical Formulation of the Investigational Polypeptide Marine Anticancer Agent Kahalalide F", *Drug Development and Industrial Pharmacy*, vol. 27, No. 8, pp. 767-780 (2001).

U.S. Appl. No. 10/570,734, filed Mar. 6, 2006, Fernando Albericio Palomera.

U.S. Appl. No. 11/587,177, filed Oct. 19, 2006, Andres Francesch Solloso.

Vippagunta et al. Crystalline solids. Adv Drug Deliv Rev May 16, 2001; 48(1):3-26 . Review.

Gura. Cancer Models-Systems for identifying new drugs are often faulty. Science 278, 1041-2 (Nov. 7, 1997).

Faircloth G et al., "Preclinical development of kahalalide F, a new marine compound selected for clinical studies," Proceedings of the American Association for Cancer Research Annual, No. 41, Mar. 2000, pp. 600-601, XP001097542, 91st Annual Meeting of the American Association for Cancer Research, San Francisco CA, USA; Apr. 1-5, 2000, Mar. 2000 ISSN: 0197-016X.

Luber-Narod J et al., "Evaluation of the use of in vitro methodologies as tools for screening new compounds for potential in vivo toxicity." Toxicology In Vitro, vol. 15, No. 4-5, Aug. 2001, pp. 571-577, XP002225749, ISSN:: 0887-2333, p. 576, col. 2, paragraph 2.

Brown Alan P et al., "Preclinical toxicity studies of kahalalide F, a new anticancer agent: single and multiple dosing regimens in the rat." Cancer Chemotherapy and Pharmacology. Germany Oct. 2002, vol. 50, No. 4, Oct. 2002, pp. 333-340, XP002225750 ISSN: 0344-5704 abstract.

Goodman & Gilman's, The Pharmacological Basis of Therapeutics, Ninth Edition, McGraw Hill, New York (1996), Section X, Chemotherapy of Neoplastic Diseases, pp. 1225-1229.

Hamann, Mark Todd, Ph.D., University of Hawaii (1992), "Biologically Active Constituents of Some Marine Invertebrates," UMI Dissertation Services, published Oct. 1993.

Merck Manual, 11th ed., pp. 456-459, 761-763, and 1368-1371; published 1969.

Lee Y S et al., "A convergent liquid-phase synthesis of salmon calcitonin" Journal of Peptide Research, Munksgaard International Publishers, Copenhagen DK, vol. 54, No. 5, Oct. 1999, pp. 328-335, XP000849313 ISSN: 1397-002X, figure 1.

Lopez-Macia et al., "Synthesis and Structure Determination of Kahalalide F." J. Am. Chem. Soc., vol. 123, No. 46, pp. 11398-11401, published on web Oct. 27, 2001.

U.S. Appl. No. 10/531,533, filed Apr. 25, 2006, Glynn Faircloth.

U.S. Appl. No. 10/546,758, Aug. 24, 2005, Miguel Angel Izquierdo Delso.

U.S. Appl. No. 10/492,670, filed Nov. 3, 2004, Jose Jimeno.

U.S. Appl. No. 10/399,571, filed Nov. 14, 2003, Glynn Faircloth.

U.S. Appl. No. 10/642,006, filed Aug. 14, 2003, Paul Scheuer.

U.S. Appl. No. 11/587,177, filed Oct. 19, 2006, Andres Francesch Solloso.

U.S. Appl. No. 11/950,144, filed Dec. 4, 2007, Miguel Angel Izquierdo Delso.

Schellens et al., "Phase I and Pharmacokinetic Study of Kahalalide F in Patients with Advanced Androgen Resistant Prostate Cancer," American Society of Clinical Oncology, May 18-21, 2002, vol. 21, part 1 of 2, p. 113a.

Schellens et al., "Phase I and Pharmacokinetic Study of Kahalalide F in Patients with Advanced Androgen Refractory Prostate Cancer," AACR-NCI-EORTC International Conference, 2001.

Suggitt et al., "50 Years of Preclinical Anticancer Drug Screening: Empirical to Target-Driven Approaches," Clinical Cancer Research, vol. 11, Feb. 1, 2005, pp. 971-981.

English translation: Angel Lopez i Macia, Ph.D. Thesis, Department de Quimica Organica. Facultat de Quimica Divisio de Ciencies Experimentals i Matematiques, Universitat de Barcelona, catalogued Jan. 18, 2001, chapters 3, 4, and Conclusion.

U.S. Appl. No. 12/019,705, filed Jan. 25, 2008, Faircloth et al.

* cited by examiner

KAHALALIDE F AND RELATED COMPOUNDS

The present invention relates to kahalalide compounds, and in particular to kahalalide F and related compounds, as well as a synthetic route for such compounds.

BACKGROUND OF THE INVENTION

Kahalalide F is a bioactive cyclic depsipeptide isolated from the sarcoglossan mollusc *Elysia rufescens* and its diet, the green alga *Bryopsis* sp. Kahalalide F was first isolated by Hamann and Scheuer, see Hamann, M. T.; Scheuer, P. J. J. Am. Chem. Soc. 1993, 115, 5825-5826. In this publication, the absolute stereochemistry of individual valines (3 D-Val and 2 L-Val) and of threonines (L-Thr and D-allo-Thr) was not determined. In a later publication, Scheuer et al. (Goetz, G.; Yoshida, W. Y.; Scheuer, P. J. Tetrahedron 1999, 55, 7739-7746) assigned a position in the molecule for the 5 Val and the 2 Thr.

Thus, the structure for Kahalalide F according to Scheuer et al. was:

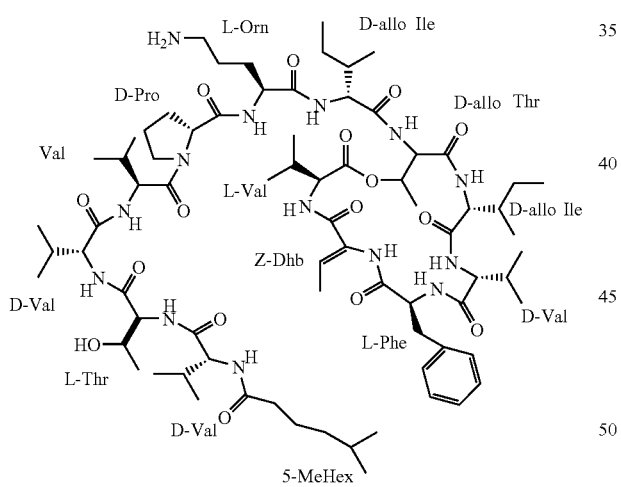

In the meantime, Prof. Reinhart also assigned the individual position of the 5-Val and the 2-Thr (K. L. Rinehart, personal communication) While for the 2 Thr and 3 Val, his assignment concords with that of Prof. Scheuer, for the last 2 Val there is a discrepancy. Thus, in the Rinehart assignment, the two consecutive Val in the side chain are switched and the structure is of the formula (I):

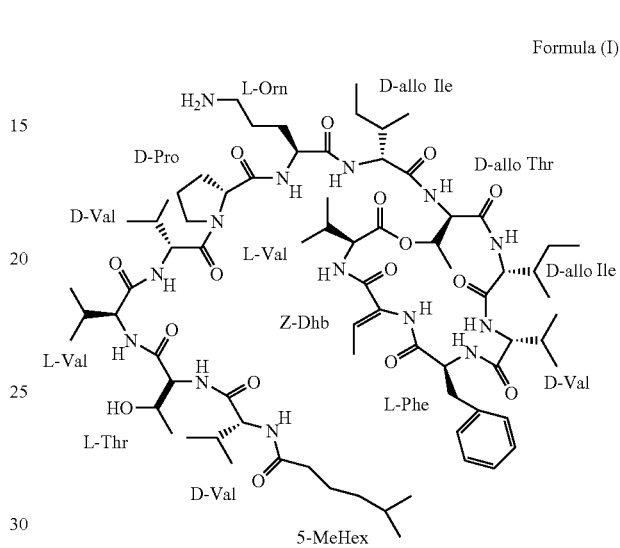

Formula (I)

It is now accepted, and demonstrated again in this text, that the correct formula for kahalalide F is the formula (I).

The structure is complex, comprising six amino acids as a cyclic part, and an exocyclic chain of seven amino acids with a terminal acyl group. Kahalalide F (I) is an exceedingly potent and rare marine-derived antitumour agent, though the absence of adequate quantities has slowed plans for clinical trials.

Other kahalalide compounds are known, and for example we refer to Hamann, M. T., et al., *J. Org. Chem.*, 1996, "Kahalalides: Bioactive Peptides from Marine Mollusk Elysia rufescens and its Algal Diet *Bryopsis* sp.", vol. 61, pp. 6594-6660. As well as kahalalide F, this article gives structures for kahalalides A to E. Kahalalide K was reported in J Nat. Prod. 1999, 62, 1169, and kahalalide O was reported in J Nat Prod 2000, 63, 152.

The structures for these further kahalalide compounds are shown in the following formulae:

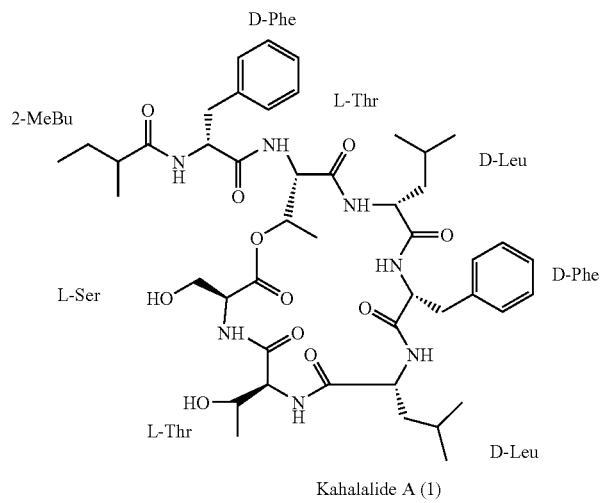
Kahalalide A (1)
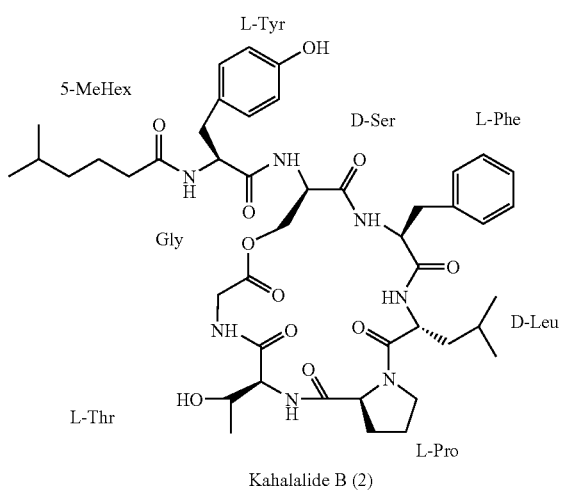
Kahalalide B (2)
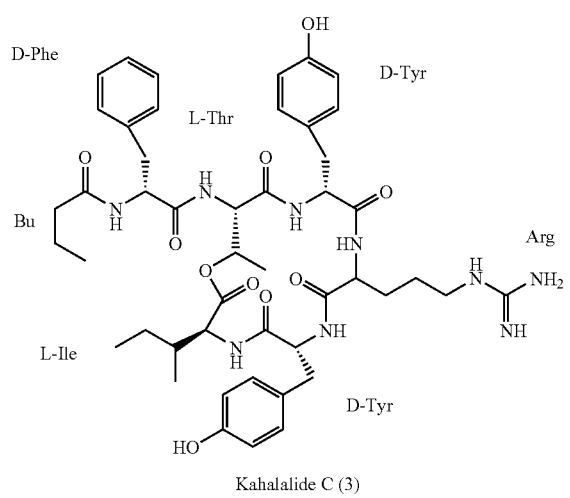
Kahalalide C (3)
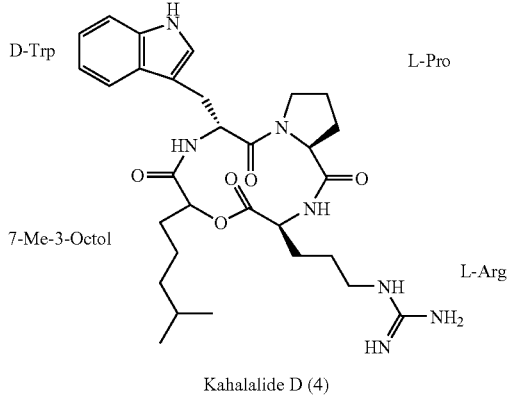
Kahalalide D (4)
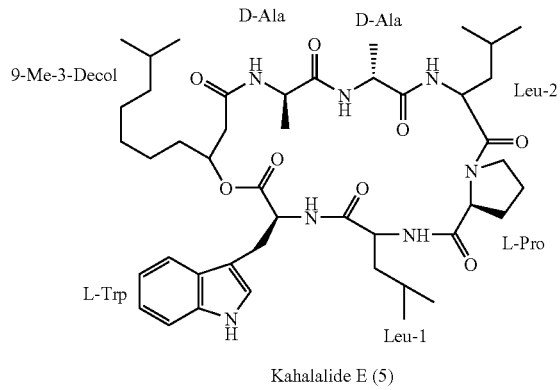
Kahalalide E (5)
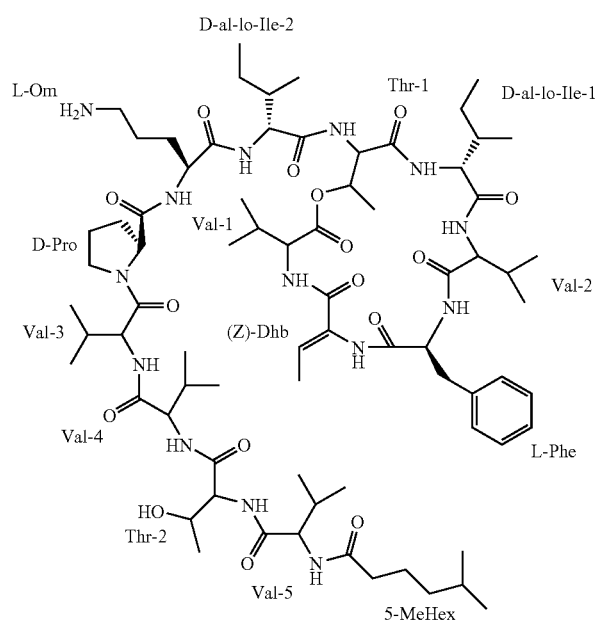
Kahalalide F (6)

-continued
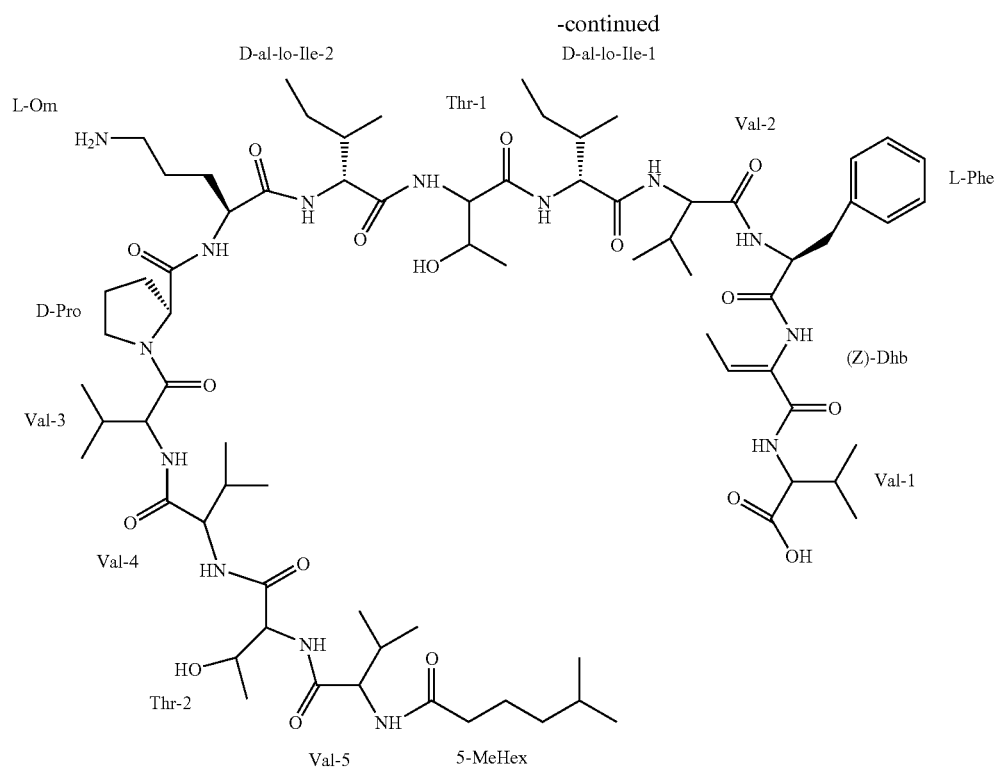
Kahalalide G (7)
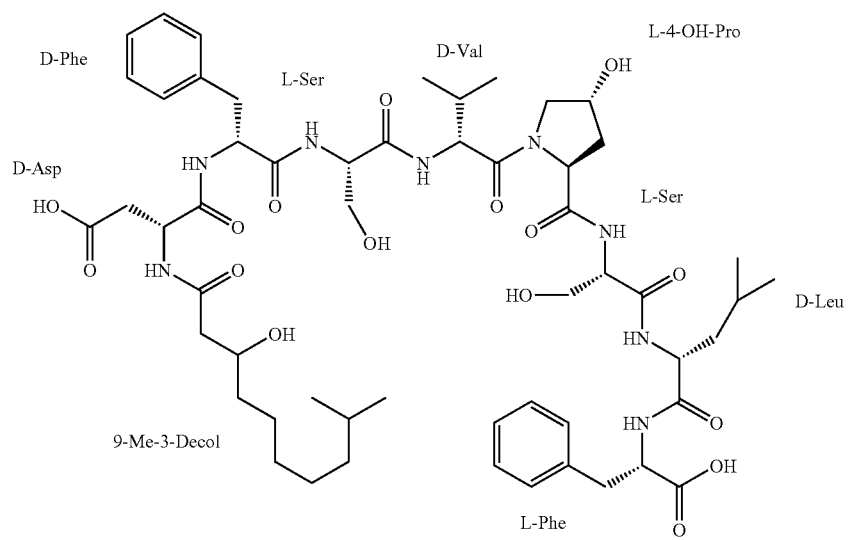
Kahalalide H (8)

-continued

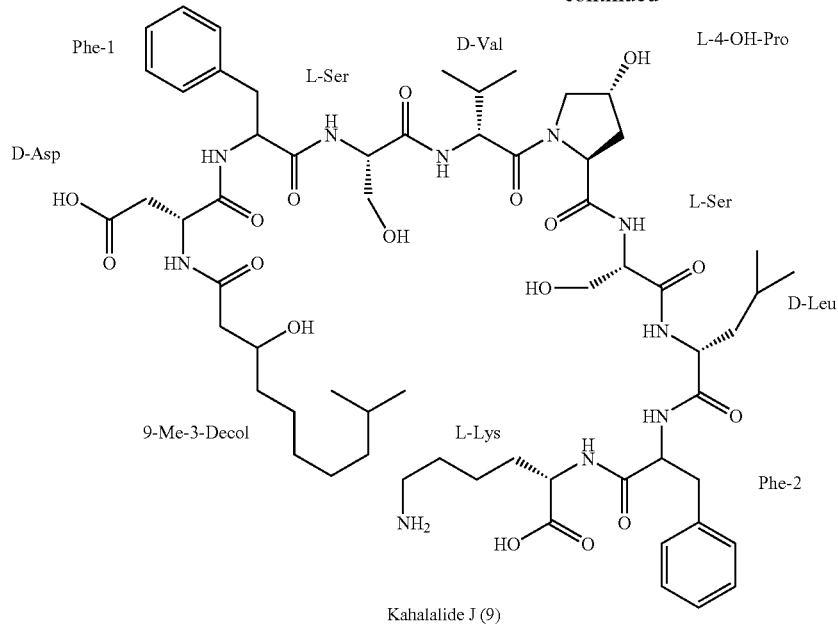

Kahalalide J (9)

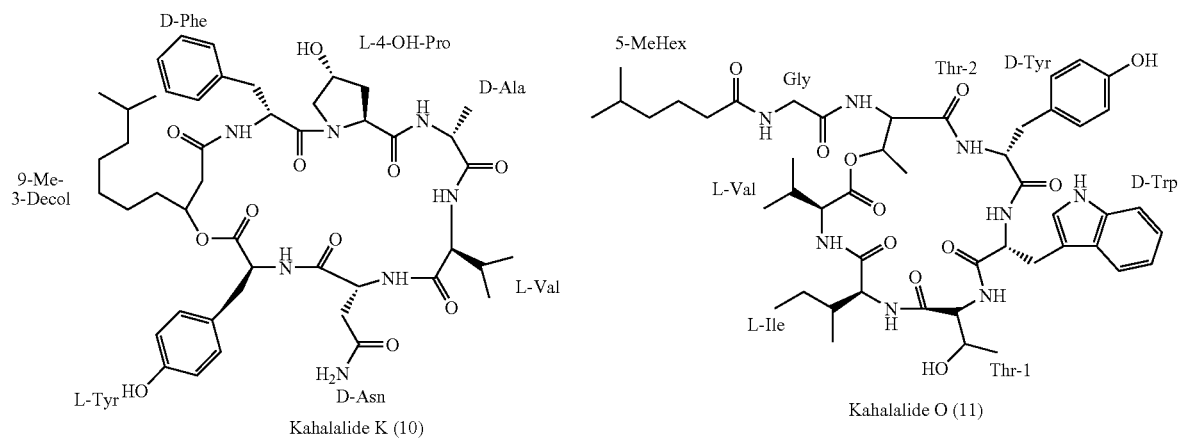

Kahalalide K (10)

Kahalalide O (11)

The cyclic kahalalides have a ring of amino acids, and a side chain which terminates in an acyl group.

Kahalalides have a range of biological activities, notably antitumour and antituberculosis activity.

SUMMARY OF THE INVENTION

The present invention provides mimics of natural kahalalides. The compounds may differ in one or more amino acids, and one or more components of the acyl side chain.

Suitably the mimics of this invention have at least one of the following features to differentiate from a parent naturally occurring kahalalide:

1 to 7, especially 1 to 3, more especially 1 or 2, most especially 1, amino acid which is not the same as an amino acid the parent compound;

1 to 10, especially 1 to 6, more especially 1 to 3, most especially 1 or 2, additional methylene groups in the side chain acyl group of the parent compound;

1 to 10, especially 1 to 6, more especially 1 to 3, most especially 1 or 2, methylene groups omitted from the side chain acyl group of the parent compound;

1 to 6, especially 1 to 3, more especially 1 or 3, substituents added to or omitted from the side chain acyl group of the parent compound.

For cyclic kahalalides, the amino acid addition or omission can be in the cyclic ring or in the side chain.

Examples of this invention are compounds related to kahalalide F, and having the formula:

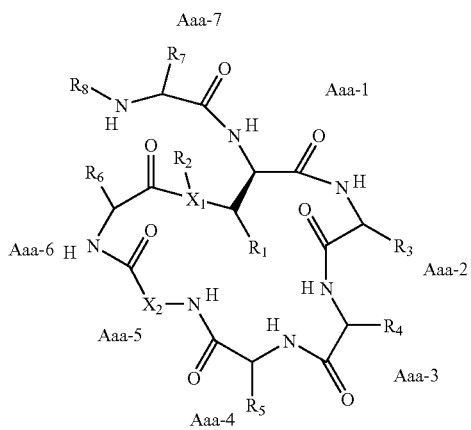

Formula II wherein Aaa₁, Aaa₂, Aaa₃, Aaa₄, Aaa₆, and Aaa₇ are independently α-amino acids of L or D configuration, if applies; wherein $R_1$, $R_2$, $R_3$, $R_4$, $R_5$, $R_6$, $R_7$ are each independently H or an organic group selected from the group consisting of an alkyl group, an aryl group, an aralkyl group, and their substituted derivatives with an hydroxy group, a mercapto group, an amino group, a guanidino group, a halogen group; wherein $X_1$ is independently O, S, or N; wherein $R_2$ is, if applies, independently H or an organic group selected from the group consisting of an alkyl group and an aralkyl group; wherein Aaa₅ is independently an amino acid of L or D configuration, if applies; wherein $X_2$ is independently an organic group selected from the group consisting of an alkenyl, an alkyl group, an aryl group, an aralkyl group, and their substituted derivatives with an hydroxy group, a mercapto independently H or an organic group selected from the group consisting of an alkyl group, an aryl group, an aralkyl group, and their substituted derivatives with an hydroxy group, a mercapto group, an amino group, a guanidino group, a halogen group; wherein $R_8$ is independently of the following formulae III, IV, or V:

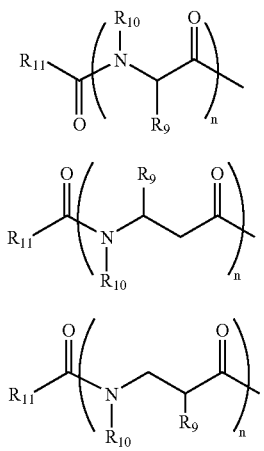

Formula III

Formula IV

Formula V wherein $R_9$, $R_{10}$, and $R_{11}$ are each independently H or an organic group selected from the group consisting of an alkyl group, an aryl group, an aralkyl group, and their substituted derivatives with an hydroxy group, a mercapto group, an amino group, a guanidino group, a carboxyl group, a carboxamido group, a halogen group; $R_9$ and $R_{10}$ can form part of the same cycle; $R_9$ can confer S or R configuration, if applies, to the carbon attached to; and n is 0 to 6. The definitions of the amino acids can also be varied to allow for proline and analogous amino acids including hydroxyproline. The formulae (III), (IV) and (V) can be intermixed to give a side chain made up of repeat units in more than one of these formulae.

In a modification, one or more of the ring amino acids Aaa-6 and Aaa-5 of the hexamino acid cycle is omitted or an amino acid Aaa-7 is added between Aaa-6 and Aaa-1, in order to arrive at rings having four, five or seven ring amino acids. Six ring amino acids is preferred.

The present invention is further directed to a synthetic process for the formation of Kahalalide F compounds and related structures.

PREFERRED EMBODIMENTS

Preferred compounds are related to Kahalalide F (I), wherein in the formula (II), Aaa-1 is D-allo-Thr ($X_1$=O, $R_1$=CH₃), Aaa-2 is D-allo-Ile ($R_3$=1-methylpropyl), Aaa-3 is D-Val ($R_4$=isopropyl), Aaa-4 is Phe ($R_5$=benzyl), Aaa-5 is Z-Dhb ($X_2$=C=CHCH₃ with Z configuration), Aaa-6 is L-Val ($R_6$=isopropyl), Aaa-7 is D-allo-Ile ($R_7$=1-methylpropyl), and $R_8$ contains a hexapeptide derivative of the following formula (Formula VI):

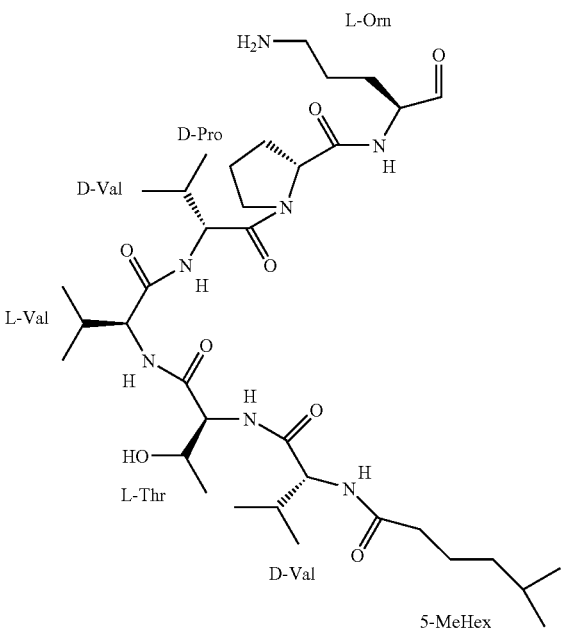

Formula VI

Other preferred compounds are analogously related to the other kahalalides, and have amino acids and side chains in common with such compounds. Reference is made to the known structures of the kahalalides. For preference, a compound of this invention mimics a natural kahalalide, with modification, insertion or suppression at one or more points in the molecule.

Especially preferred are compounds which have the same amino acids as in a natural cyclic kahalalide compound, but differ in the side chain, especially in the acyl part. Such differences can include more or fewer methylene groups, typically at most a change of two methylene groups, and more or less substituents, notably the addition of halogen such as fluorine substituents.

As used herein, the term "organic group" means a hydrocarbon group that is classified as an aliphatic group, cyclic group, or combination of aliphatic and cyclic groups (e.g., aralkyl groups). In the context of the present invention, the term "aliphatic group" means a saturated or unsaturated linear or branched hydrocarbon. This term is used to encompass alkyl, alkenyl, and alkynyl groups, for example.

The term "alkyl group" means a saturated linear or branched hydrocarbon group including, for example, methyl, ethyl, isopropyl, isobutyl, t-butyl, heptyl, dodecyl, octadecyl, amyl, 2-ethylhexyl, 2-methylbutyl, 5-methylhexyl, 9-methyl-3-decyl, and the like, particularly alkyl groups which have a single branched methyl group. Suitably the alkyl group is long and has 1 to 20 carbon atoms, more typically 1 to 15 or 1 to 10 carbon atoms, or can be short and has 1 to 6 or 1 to 3 carbon atoms. The group $R_{11}$ is suited to the long carbon chains, and in general all the other alkyl groups are preferably short.

The term "alkenyl group" means an unsaturated, linear or branched hydrocarbon group with one or more carbon-carbon double bonds, such as a vinyl group. Suitably the alkenyl group has 2 to 8 or 2 to 4 carbon atoms.

The term "alkynyl group" means an unsaturated, linear or branched hydrocarbon group with one or more carbon-carbon triple bonds. Suitably the alkynyl group has 2 to 8 or 2 to 4 carbon atoms.

The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups, and is suitably a mono- or bi-cycle with 4 to 10 carbon atoms. The term "aromatic group" or "aryl group" means a mono- or polycyclic aromatic hydrocarbon group, suitably a mono- or bi-cycle with 5 to 10 carbon atoms. The term "heterocyclic group" means a closed ring hydrocarbon in which one or more of the atoms in the ring is an element other than carbon (e.g., 1 to 3 of one or more of nitrogen, oxygen, sulfur, etc.), suitably a mono- or bi-cycle with 4 to 10 ring atoms.

As is well understood in this technical area, a large degree of substitution is not only tolerated, but is often advisable. Substitution is anticipated on the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl group or other conventional substitution. Where the term "moiety" is used to describe a chemical compound or substituent, only a unsubstituted chemical material is intended to be included. For example, the phrase "alkyl group" is intended to include not only pure open chain saturated hydrocarbon alkyl substituents, such as methyl, ethyl, propyl, isobutyl, and the like, but also alkyl substituents bearing further substituents known in the art, such as hydroxy, alkoxy, amino, carboxyl, carboxamido, halogen atoms, cyano, nitro, alkylsulfonyl, etc. Thus, "alkyl group" includes ether groups, haloalkyls, alcohols, thiols, carboxyl, amines, hydroxyalkyls, sulfoalkyls, etc. Haloalkyl groups are currently preferred. On the other hand, the phrase "alkyl moiety" is limited to the inclusion of only pure open chain saturated hydrocarbon alkyl substituents, such as methyl, ethyl, propyl, isobutyl, and the like.

In a particularly preferred embodiment of this invention, we provide a compound of the formula (A):

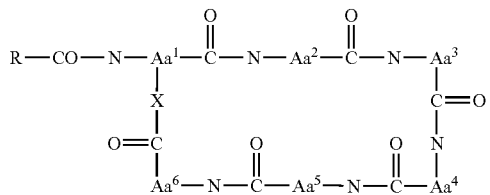

where each of $Aa^1$ to $Aa^6$ with the adjacent respective —N— and —CO— represents an α or β amino acid, preferably an a amino acid, X is a linking group of $Aa^1$, preferably selected from amino, hydroxy or thiol, more preferably hydroxy, and R is a group optionally including one or more α or β amino acids, preferably α amino acids. In a variation, —CO-$Aa^6$-N— may be absent, possibly along with —CO-$Aa^5$-N— also being absent, or alternatively a group —CO-$Aa^7$-N— may be interposed between $Aa^6$ and $Aa^1$.

The amino acids can be of L or D configuration. Preferably the configuration is the same as the corresponding amino acid in a kahalalide comound especially kahalalide F. One or more of $Aa^1$ to $Aa^7$ preferably corresponds to an amino acid at the same position in a natural kahalalide, or a congener thereof. In a particularly preferred embodiment, each amino acid is the same as in kahalalide F. Thus, for preference, $Aa^1$ is D-allo-Thr, $Aa^2$ is D-allo-Ile, $Aa^3$ is D-Val, $Aa^4$ is Phe, $Aa^5$ is Z-Dhb, $Aa^6$ is L-Val.

Where congeners are employed, suitable congeners have substitute amino acids where the substitution is made having regard to the structure of the respective amino acid in the natural kahalalide such as kahalalide F. Substitutes for threonine include serine and other homologues as well as cysteine and homologues. Substitutes for isoleucine include other amino acids with nonpolar groups, including alanine, valine, leucine, and proline, as well as analogues and homologues. In this respect, the showing of the nitrogen atoms —N— in the formula (A) does not exclude the possibility of ring formation such as occurs with proline. Substitutes for valine include isoleucine and the other amino acids with nonpolar groups, including analogues and homologues. Substitutes for phenylalanine include tryptophan and tyrosine. Substitutes for Dhb include other amino acids with such an alkenylidene substituent, including amino acids with $C_3$ or higher sidechains, as well as analogues and homologues.

Preferably $Aa^1$ is of the formula:

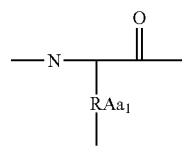

where $Raa_1$ is a sidechain carrying the linking X. Examples of sidechains include alkyl, aryl and aralkyl, especially alkyl, more typically alkyl of 1 to 4, such as 2 carbon atoms. Branched alkyl is preferred. The linking group X is suitably oxygen, with $Aa_1$ being preferably derived from threonine, but sulphur, amino (unsubstituted or substituted with alkyl, aryl or aralkyl), and other linkers can be employed. Suitably the group X is the only polar group in $Aa^1$. $Aa^1$ can be racemic, L or D, but is preferably in the D configuration.

Preferably $Aa^2$ is of the formula:

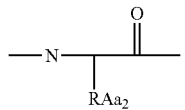

where $Raa_2$ is a sidechain such as alkyl, aryl and aralkyl, especially alkyl, more typically alkyl of 1 to 5, such as 3 carbon atoms. Branched alkyl is preferred, as in isoleucine. Suitably there are no polar substituents in $Aa^2$. $Aa^2$ can be racemic, L or D, but is preferably in the D configuration.

Preferably $Aa^3$ is of the formula:

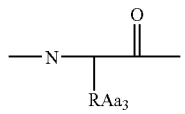

where $Raa_3$ is a sidechain such as alkyl, aryl and aralkyl, especially alkyl, more typically alkyl of 1 to 5 such as 3 carbon atoms. Branched alkyl is preferred, as in valine. Suitably there are no polar substituents in $Aa^3$. $Aa^3$ can be racemic, L or D, but is preferably in the D configuration.

Preferably $Aa^4$ is of the formula:

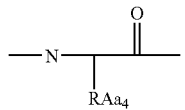

where $Raa_4$ is a sidechain such as alkyl, aryl and aralkyl, especially aralkyl, more typically aralkyl of 7 to 10 such as 7 carbon atoms. Benzyl is preferred, as in phenylalanine. Suitably there are no polar substituents in $Aa^4$. $Aa^4$ can be racemic, L or D, but is preferably in the L configuration.

Preferably $Aa^5$ is of the formula:

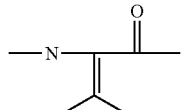

where $Raa_{5a}$ and $Raa_{5b}$ is each chosen from hydrogen, or a sidechain such as alkyl, aryl and aralkyl, especially alkyl, more typically alkyl of 1 to 4 such as 1 carbon atom. Preferably $Raa_{5a}$ is hydrogen, giving a Z configuration as in the preferred a,b-didehydro-a-aminobutyric acid. Suitably there are no polar substituents in $Aa^5$. $Aa^5$ can be racemic, L or D, but is preferably in the L configuration.

Preferably $Aa^6$ is of the formula:

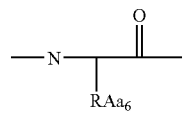

where $Raa_6$ is a sidechain such as alkyl, aryl and aralkyl, especially alkyl, more typically alkyl of 1 to 5 such as 3 carbon atoms. Branched alkyl is preferred, as in valine. Suitably there are no polar substituents in $Aa^6$. $Aa^6$ can be racemic, L or D, but is preferably in the L configuration.

The amino acids $Aa^1$ to $Aa^7$ can be as defined for the groups Aaa-1 to Aaa-7 of formula (II).

Preferably the side chain R comprises 5-MeHex-D-Val-L-Thr-L-Val-D-Val-D-Pro-L-Orn-D-allo-Ile, or a congener thereof, including analogues and homologues. Examples of congeners include those of the general formula $(R^t)_m$-(amino acid)$_n$-, with m+n non-zero, where $R^t$ represents a terminal group, suitably an alkyl, alkenyl, alkynyl, aryl, aralkyl, heteroaryl, heteroalkyl, alicyclic or other terminator, and -(amino acid)$_n$- repersents an optional chain of amino acids.

A terminal alkyl group suitably has 1 to 12 carbon atoms, more typically 4 to 10 carbon atoms, and may be substituted and is preferably branched. Examples include butyl, pentyl, hexyl, heptyl, octyl, and other alkyl groups bearing 1 or more methyl or ethyl or longer side groups preferably of 1 to 6 carbon atoms, especially 5-methylhexyl and other alkyl groups with branching distal to the point of attachment to the rest of the molecule. Suitable substituents include halogen, hydroxy, alkoxy, amino, carboxyl, carboxamido, cyano, nitro, alkylsulfonyl, alkoxy, alkoxyalkyl, arylalkylaxyl, heterocyclic, alicyclic, aryl, aralkyl and other groups mentioned herein. As appropriate, such substituents may bear further substituents, as for example a tolyl group. Halogen substituents are currently most preferred, especially 1 or more, such as 1 to 3, flourine atoms. Other terminal groups can be selected according to the guidance given in this text, and include alicyclic, aralkyl, aryl, heterocyclic or other groups, possibly with 1 or more, especially 1 to 3, susbtituents.

The side chain R—CO—N— can have hydrogen or a substituent on the nitrogen, such as alkyl, aryl or aralkyl group.

Suitable side chain congeners employ substitute amino acids chosen in accordnace with the principles given before, with alternatives to isoleucine, valine and threonine being selected as for these amino acids in the cyclic part of the molecule, and alternatives to ornithine inclluding lysine, histidine, arginine; alternatives to proline including alanine and other nonpolar amino acids such as glycine, isoleucine and the others previously mentioned. Typically the chain R has 0 to 10, more preferably 4 to 8, such as 5, 6 or 7, especially 7, amino acid residues. Where there are more than seven amino acids, then the extra amino acids are preefrably naturally occuring amino acids, particularly those mentioned herein.

Racemic or L or D amino acids can be used. Preferably where amino acids are present in the side chain R, then one or more of them is in the configuration given for the naturally occuring sidechain. Reading from the cylic hexapeptide, the amino acid residues are in the configuration DLDDLLD. The terminal alkyl group suitably has 1 to 12 carbon atoms, more typically 4 to 10 carbon atoms, and may be substituted and is preferably branched. Suitable substituents include halogen, hydroxy, alkoxy, amino, carboxyl, carboxamido, cyano, nitro, alkylsulfonyl and other groups mentioned herein. Halogen substituents are current most preferred.

More generally, the side chain R—CO—N— can be as defined for the side chain $R_8$—NH—$CHR_7$—CO—NH— in the compounds of formula (II), including compounds with mixtures of amino acids defined within formulae (III), (IV) and (V).

Although the preferrred features have been described by reference to kahalalide F, other preferred compounds of this invention are provided by the application of the same principles to the design of mimics of other kahalalides. Thus, the amino acids and side chains can be changed, preferably while retaining the hydrophobic-hydrophilic balance between polar and nonpolar groupings.

Compounds of this invention have useful biological activity, including an antitumour activity.

Thus, the present invention provides a method of treating any mammal, notably a human, affected by cancer which comprises administering to the affected individual a therapeutically effective amount of a compound of the invention, or a pharmaceutical composition thereof.

The present invention also relates to pharmaceutical preparations, which contain as active ingredient a compound or compounds of the invention, as well as the processes for their preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the ecteinascidins such as ecteinascidin 743 or the didemnins such as aplidine;

m) steroid analogues, in particular dexamethasone;

n) anti-inflammatory drugs, in particular dexamethasone; and o) anti-emetic drugs, in particular dexamethasone.

The present invention also extends to the compounds of the invention for use in a method of treatment, and to the use of the compounds in the preparation of a composition for treatment of cancer.

Compounds of this invention are also expected to have antituberculosis activity.

According to this invention there is also provided a process for preparing compounds of this invention including kahalalide F, which comprises ring closing between $Aa_3$ and $Aa_4$. We have found that ring closing at this position gives a superior process. Ring closing can be preceded and/or followed by other modifications to the molecule, including forming or extending the side chain on $Aa_1$, and/or removing protecting groups and/or modifying substituents on the amino acids.

Thus, the process can be illustrated by the following scheme:

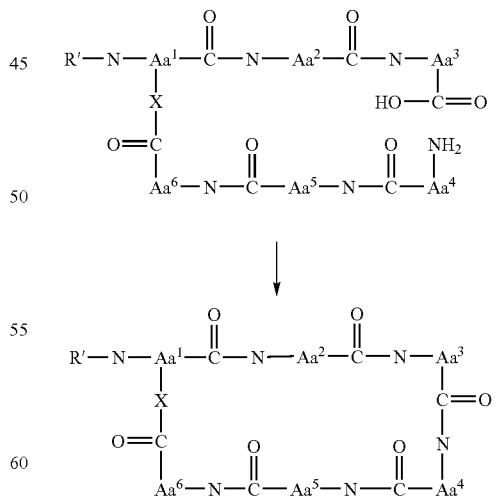

where R' is a group R—CO—or a precursor therefor, and where one or more of the amino acids may have protecting groups, and where the —COOH of $Aa^3$ and/or the —$NH_2$ of $Aa^4$ may optionally be protected, activated or derivatised.

Such procedures using precursors or of protection, activation or derivatisation are in themselves entirely conventional, and further details are not needed to practice the process.

The process of this invention can be carried out from starting materials in an enantio- and stereocontrolled and fast manner, taking advantages of the solid-phase synthetic methodology, where the molecule in construction is bounded to an insoluble support during all synthetic operations. Thus, excess of reagents and soluble by-products can be removed simply by washing the molecule-resin with suitable solvents. Large excesses of the soluble reagents can, therefore, be used in order to drive the reactions to completion in a short period of time, avoiding racemization (if applies) and other secondary reactions. The method is also amenable for automation.

The preferred embodiment of the synthetic process of the present invention is best represented in the Scheme 1, which is directed to the formation of compounds of the formula (II).

Scheme 1

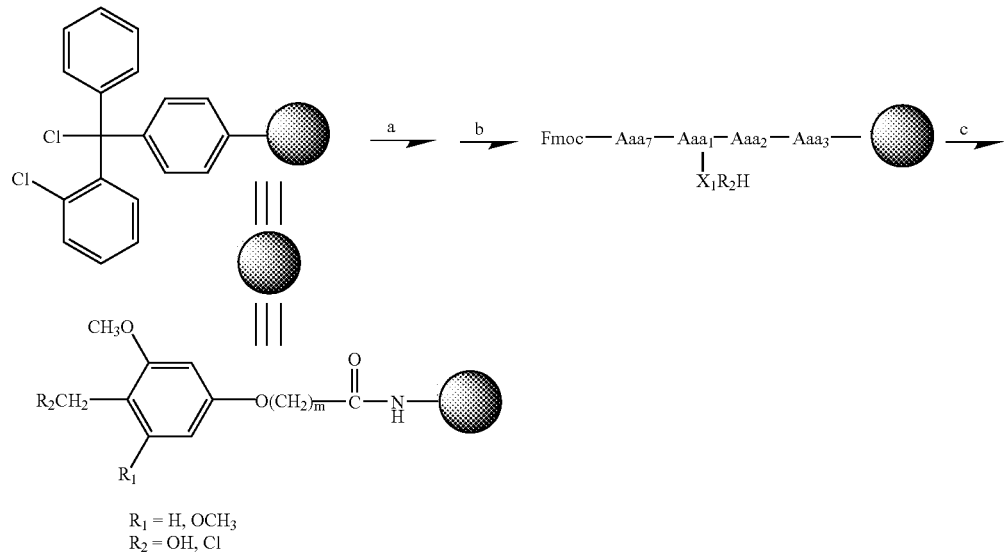

$R_1 = H, OCH_3$
$R_2 = OH, Cl$

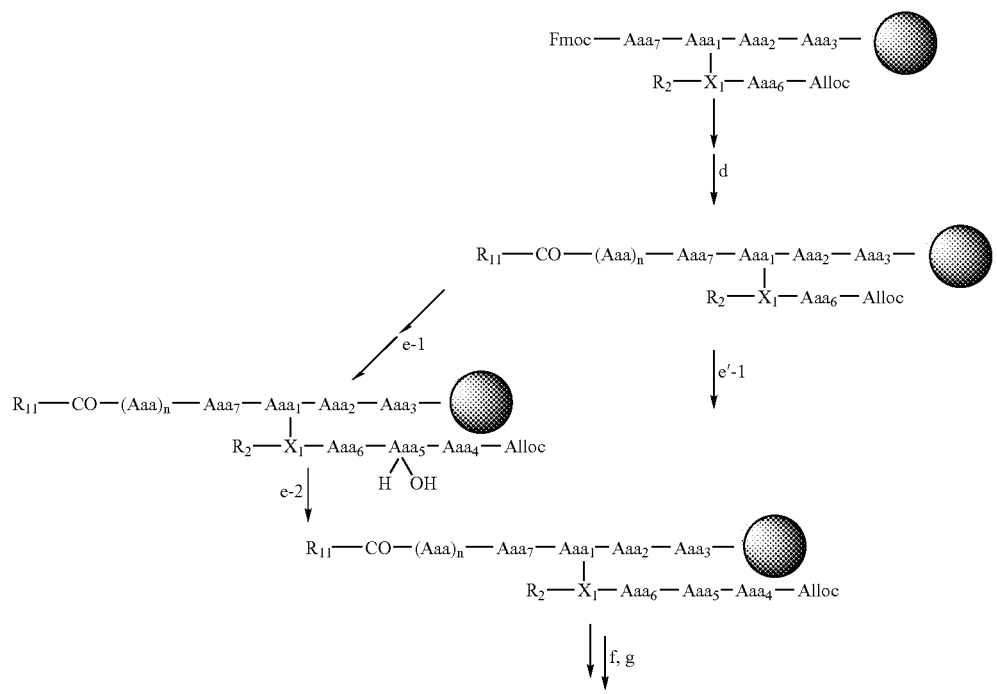

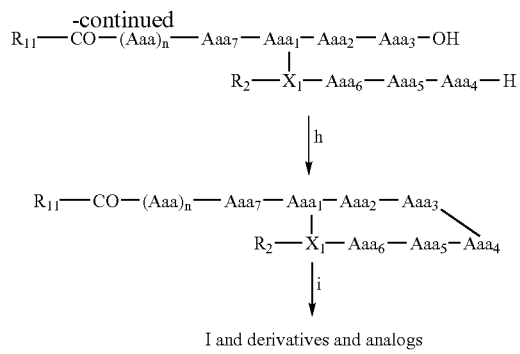

I and derivatives and analogs

As shown above in Scheme 1, the preferred process for the synthetic formation of Kahalalide F (I) and derivatives and analogues is based in a solid-phase approach, see for example Lloyd-Williams, P., et al., *Chemical Approaches to the Synthesis of Peptides and Proteins*, CRC Press, Boca Raton (FL), 1997.

The process of Scheme 1 comprises the sequential steps of:
(a) incorporating an Fmoc-amino acid (Aaa$_3$) onto a solid support (e.g., polystyrene, polyethylene grafted on polystyrene, and the like) containing a super-acid labile handle or linker (e.g., chlorotrityl, polyalkoxybenzyl, and the like) forming an ester bond;
(b) elongating the peptidic chain with three amino acids (Aaa$_2$, Aaa$_1$, Aaa$_7$) using a Fmoc/tBu strategy. For I, X$_1$=OH and introduced without protection. When X$_1$=NH$_2$, this is introduced with Alloc protection;
(c) incorporating (Aaa$_6$) using an Alloc/tBu strategy;
(d) elongating the peptidic chain with the remaining amino acids and R$_{11}$—COOH through Aaa$_7$ using a Fmoc/tBu strategy;
(e-1) elongating the peptidic chain with two amino acids [Aaa$_5$ (OH,H), Aaa$_4$] through Aaa$_6$ using an Alloc/tBu strategy. The OH attached to Aaa$_5$ is unprotected;
(e-2) dehydrating in solid-phase to give the peptide with Aaa$_5$; or
(e'-1) incorporating the dipeptide Alloc-Aaa$_4$-Aaa$_5$-OH, which has been combined and dehydrated in solution;
(f) removing the Alloc group of Aaa$_4$ while the peptide is still anchored to the solid support;
(g) cleaving the side-chain protected, if applies, peptide from the solid support;
(h) cyclizing the peptide in solution;
(i) removing TFA labile side chain protecting groups.

It will be appreciated that the particular choice of protecting groups is not critical, and other choices are widely available. For example, Bzl type groups can replace tBu/Boc; Boc instead of Fmoc; Fmoc instead of Alloc; Wang resin instead of chlorotrityl.

DETAILED DESCRIPTION OF THE PREFERRED EMBODIMENTS OF THE PROCESS

The preferred process of the present invention is illustrated in Scheme 1. As shown therein, and as discussed in greater detail in the examples which follow below, this process was conducted as follows:

Fmoc-Aaa$_3$-OH was incorporated preferably to a chlorotrityl-polystyrene resin, see Barlos, K.; Gatos, D.; Schafer, W. Angew. Chem. Int. Ed. Engl. 1991, 30, 590-593, in the presence of DIEA keeping the level of substitution of aprox. 0.15-0.5 mmol/g. The use of higher loadings brings the presence of terminated peptides in the final product, see Chiva, C.; Vilaseca, M.; Giralt, E.; Albericio, F. J. Pept. Sci. 1999, 5, 131-140.

Removal of the Fmoc group was carried out with piperidine-DMF (2:8, v/v) (1×1 min, 3×5 min, 1×10 min). Couplings of Fmoc-, Alloc-Aaa-OH, and R11—COOH (5 equiv) were carried out with HATU-DIEA, see Carpino, L. A.; El-Faham, A.; Minor, C. A.; Albericio, F. J. Chem. Soc., Chem. Commun. 1994, 201-203, (5:10) in DMF for 90 min. After the coupling ninhydrin test was carried out and if it was positive the coupling was repeated in the same conditions, otherwise the process was continued. Washings between deprotection, coupling, and, again, deprotection steps were carried out with DMF (5×0.5 min) and CH2Cl2 (5×0.5 min) using each time 10 mL solvent/g resin.

Incorporation of Alloc-Aaa$_6$-OH (7 equiv) when X1=O was carried with equimolar amount of DIPCDI and 0.7 equiv of DMAP for 2 h. This coupling was repeated twice.

Removal of Alloc group was carried out with Pd(PPh3)4 (0.1 equiv) in the presence of PhSiH3 (10 equiv) under atmosphere of Ar, see Gómez-Martinez, P.; Thieriet, N.; Albericio, F.; Guibé, F. J. Chem. Soc. Perkin I 1999, 2871-2874.

Dehydration was carried out in solid-phase with EDC (water soluble carbodiimide, 100 equiv) in the presence of CuCl (60 equiv) in CH2Cl2-DMF (10:2) for 6 days. EDC/CuCl has been used by dehydration in solution of a residue of Thr in a fragment of Nisin. Fukase, K.; Kitazawa, M.; Sano, A.; Shimbo, K.; Horimoto, S.; Fujita, H.; Kubo, A.; Wakarniya, T.; Shibe, A. Bull. Chem. Soc. Jpn. 1992, 65, 2227-2240.

The dipeptide Alloc-Aaa$_4$-Aaa$_5$-OH (5 equiv), which was prepared in solution from Alloc-Aaa$_4$-OH and H-Aaa$_5$(OH, H)-OtBu with EDC, and posterior dehydratation and treatment with TFA, was coupled with HATU-DIEA (5:10) for 16 h and recoupling for 3 h The use of other coupling reagents based in HOBt, such as HBTU or DIPCDI-HOBt, have led to incomplete incorporations of the dipeptide.

Cleavage of the protected peptide from the resin was accomplished by TFA-CH$_2$Cl$_2$ (1:99) (5×30 sec).

Cyclization step was carried out with DIPCDI-HOBt (3:3 equiv) in CH2Cl2-DMF for 2 hrs. Other methods, such as PyBOP/DIEA (3:6 equiv) in DMF can be also be used.

Final deprotection was carried out with TFA-H$_2$O (95:5) for 1 h.

EXAMPLES OF THE INVENTION

Abbreviations

Abbreviations used for amino acids and the designations of peptides follow the rules of the IUPAC-IUB Commission of Biochemical Nomenclature in *J. Biol. Chem.* 1972, 247, 977-983. The following additional abbreviations are used: 4-AcBut-OH, 4-acetoxybutyric acid; AcButBut-OH, 4-(4- acetoxybutanoyloxy)-butyric acid; ACH, a-cyano-4-hydroxycinnamic acid; Alloc, allyloxycarbonyl; Boc, tert-butyloxycarbonyl; t-Bu, tert-Butyl; But-OH, butyric acid; Cl-TrtCl-resin, 2-chlorotrityl chloride-resin; Dap, 2,3-diaminopropionic acid; 4-DiMeABut-OH, N,N-dimethyl-4-aminobutyric acid; 3,3-DiMeBut-OH, 3,3-Dimethylbutyric acid; DHB, 2,5-dihydroxybenzoic acid; ZDhb, a,b-Didehydro-a-aminobutyric acid; DIEA, N,N-diisopropylethylamine; DMF, N,N-dimethylformanide; EDC, 1-ethyl-3-(3'-dimethylaminopropyl)carbodiimide hydrochloride; Etg, ethylglycine; ESMS, electrospray mass spectrometry; FABMS, fast atom bombardment mass spectrometry; Fmoc, 9-fluorenylmethoxycarbonyl; HATU, N-[(dimethylamino)-1H-1,2,3-triazolo-[4,5-b]pyridin-1-yl-methylene]-N-methylmethanaminium hexafluorophosphate N-oxide; HBTU, N-[(1H-benzotriazol-1-yl)(dimethylamino)methylene]-N-methylmethanaminium hexafluorophosphate N-oxide; 2-Hedo-OH, 2,4-hexadienoic acid; Hep-OH, heptanoic acid; HOAc, acetic acid, HOAt, 1-hydroxy-7-azabenzotriazole (3-hydroxy-3H-1,2,3-triazolo-[4,5-b]pyridine); HOBt, 1-hydroxybenzotriazole; IBut-OH, isobutyric acid; 3-MeBut-OH, 3-methylbutyric acid; 5-MeHex-OH, 5-methylhexanoic acid; MeOH, methanol; 4-MePen-OH, 4-methylpentanoic acid; NMM, N-methylmorpholine; 4-HOBut, 4-hydroxybutyric; (b-OH)Phe-OH, b-hydroxyphenylalanine; Lit-OH, Litho-cholic acid; Pal, palmitic acid; D-Phe-OH, a,b-Didehydrophenylalanine; PyAOP, 7-azabenzotriazol-1-yl-N-oxy-tris(pyrrolidino)phosphonium hexafluorophosphate; PyBOP, benzotriazol-1-yl-N-oxy-tris(pyrrolidino)phosphonium hexafluorophosphate; SPS, solid-phase synthesis; TFA, trifluoroacetic acid; Tico-OH, tetraicosanoic acid. Amino acid symbols denote the L-configuration unless stated otherwise. All solvent ratios are volume/volume unless stated otherwise.

General Procedures. Cl-TrtCl-resin, Protected Fmoc-amino acid derivatives, HOBt, PYBOP, HATU were from PerSeptive Biosystems (Framingham, Mass.), Bachem (Bubendorf, Switzerland), NovaBiochem (Läufelfingen, Switzerland). Alloc-amino acids were prepared essentially as described by Dangles et al., see Dangles, O.; Guibé, F.; Balavoine, G.; Lavielle, S.; Marquet. A. J. Org. Chem. 1987, 52, 4984-4993, and 5-MeHex-OH through a malonic synthesis. DIEA, DIPCDI, EDC, Piperidine, TFA were from Aldrich (Milwaukee, Wis.). DMF and $CH_2Cl_2$ were from SDS (Peypin, France). Acetonitrile (HPLC grade) was from Scharlau (Barcelona, Spain). All comercial reagents and solvents were used as received with exception of DMF and $CH_2Cl_2$, which were bubbled with nitrogen to remove volatile contaminants (DMF) and stored over activated 4 Å molecular sieves (Merck, Darmstadt, Germany) (DMF) or $CaCl_2$ ($CH_2Cl_2$). Solution reactions were performed in round bottom flasks. Organic solvent extracts were dried over anhydrous $MgSO_4$, followed by solvent removal at reduced pressures and <40° C.

Solid-phase synthesis were carried out in polypropylene syringes (20, 10 mL) fitted with a polyethylene porous disc. Solvents and soluble reagents were removed by suction. Removal of the Fmoc group was carried out with piperidine-DMF (2:8, v/v) (1×1 min, 3×5 min, 1×10 min). Washings between deprotection, coupling, and, again, deprotection steps were carried out with DMF (5×0.5 min) and $CH_2Cl_2$ (5×0.5 min) using each time 10 mL solvent/g resin. Peptide synthesis transformations and washes were performed at 25° C. Syntheses carried out on solid-phase were controlled by HPLC of the intermediates obtained after cleaving with TFA-$H_2O$ (9:1) for 60 min an aliquot (aprox. 10 mg) of the peptidyl-resin HPLC columns [Kromasil $C_{18}$ (Conditions A-F)/$C_4$ (Conditions G,H)] reversed-phase column, 4.6×250 mm, 10 mm) were from Akzo Nobel (Bohum, Sweden). Analytical HPLC was carried out on a Shimadzu instrument comprising two solvent delivery pumps (model LC-6A), automatic injector (model SIL-6B), variable wavelength detector (model SPD-6A), system controller (model SCL-6B) and plotter (model C-R6A). UV detection was at 220 nm, and linear gradients of $CH_3CN$ (+0.036% TFA) into $H_2O$ (+0.045% TFA) were run at 1.0 mL/min flow rate from: (Condition A) 1:9 to 10:0 over 30 min; (Condition B) 3:7 to 10:0 over 30 min; (Condition C) 1:19 to 19:1 over 30 min; (Condition D) 45:55 to 90:10 over 30 min; (Condition E) 45:55 to 6:4 over 30 min; (Condition F) isocratic 1:1; (Condition G) 3:7 to 1:0 over 30 min; (Condition H) 1:1 to 1:0 over 30 min.

MALDI-TOF— and ES-MS analysis of peptide samples were performed in a PerSeptive Biosystems Voyager DE RP, using CHCA or DHB matrices, and in a Micromass VG-quattro spectrometer. Peptide-resin samples were hydrolyzed in 12 N aqueous HCl-propionic acid (1:1), at 155° C. for 1-3 h and peptide-free samples were hydrolyzed in 6 N aqueous HCl at 155° C. for 1 h. Subsequent amino acid analyses were performed on a Beckman System 6300 autoanalyzer. $^1$H-NMR (500 MHz, 200 MHz) and $^{13}$C-NMR (50 MHz) spectroscopy was performed on a Bruker DMX-500 (11.7 T) and Varian Gemini 200 (4.7 T). Chemical shifts (d) are expressed in parts per million downfield from TMS. Coupling constants are expressed in hertz.

Kahalalide F (I)

Example 1

H-D-Val-O-TrtCl-resin.

Cl-TrtCl-resin (1 g, 1.35 mmol/g) was placed in a 20 mL polypropylene syringe fitted with a polyethylene filter disk. The resin was then washed with $CH_2Cl_2$ (5×0.5 min), and a solution of Fmoc-D-Val-OH (92 mg, 0.27 mmol, 0.2 equiv) and DIEA (471 mL, 2.7 mmol, 2 equiv) in $CH_2Cl_2$ (2.5 mL) was added, and the mixture was stirred for 1 h. The reaction was terminated by addition of MeOH (800 mL), after a stirring of 15 min. The Fmoc-D-Val-O-TrtCl-resin was subjected to the following washings/treatments with $CH_2Cl_2$ (3×0.5 min), DMF (3×0.5 min), piperidine-$CH_2Cl_2$-DMF (1:9.5:9.5, 1×10 min), piperidine-DMF (1:4, 1×15 min), DMF (5×0.5 min), isopropanol (2×1 min), DMF (5×0.5 min), MeOH (2×1 min), and dried over vacuum. The loading as calculated by AAA was 0.15 mmol/g.

Example 2

Fmoc-D-allo-Ile-D-allo-Thr(Val-Alloc)-D-allo-Ile-D-Val-O-TrtCl-resin.

Fmoc-D-allo-Ile-OH (265 mg, 0.75 mmol, 5 equiv), Fmoc-D-allo-Thr-OH (free hydroxy group) (256 mg, 0.75 mmol, 5 equiv), and Fmoc-D-allo-Ile-OH (265 mg, 0.75 mmol, 5 equiv) were added sequentially to the above obtained H-D-Val-O-TrtCl-resin using HATU (285 mg, 0.75 mmol, 5 equiv) and DIEA (261 mL, 1.5 mmol, 10 equiv) in DMF (2.5 mL). In all cases, after 90 min of coupling, the ninhydrin test was negative. Removal of Fmoc group and washings were carried out as described in General Procedures. Alloc-Val-OH (211 mg, 1.05 mmol, 7 equiv) was coupled with DIPCDI (163 mg, 1.05 mmol, 7 equiv) in the presence of DMAP (12.8 mg, 0.105 mmol, 0.7 equiv). This coupling was repeated in the same conditions twice. An aliqout of the peptidyl-resin was treated with TFA-$H_2O$ (9:1) for 60 min and the HPLC (Condition A, $t_R$ 25.9 min) of the crude obtained after evaporation showed a purity of >98%. ESMS, calcd for $C_{45}H_{63}N_5O_{11}$, 849.5. Found: m/z 850.1 [M+H]$^+$.

Example 3

5-MeHex-D-Val-Thr(tBu)-Val-D-Val-D-Pro-Orn(Boc)-D-allo-Ile-D-allo-Thr(Val-Alloc)-D-allo-Ile-D-Val-O-TrtCl-resin.

The Fmoc group was removed and Fmoc-Orn(Boc)-OH (341 mg, 0.75 mmol, 5 equiv), Fmoc-D-Pro-OH (253 mg, 0.75 mmol, 5 equiv), Fmoc-D-Val-OH (255 mg, 0.75 mmol, 5 equiv), Fmoc-Val-OH (255 mg, 0.75 mmol, 5 equiv), Fmoc-Thr(tBu)-OH (298 mg, 0.75 mmol, 5 equiv), Fmoc-D-Val-OH (255 mg, 0.75 mmol, 5 equiv), and 5-MeHex-OH (98 mg, 0.75 mmol, 5 equiv) were sequentially added to the above peptidyl-resin (Example 2) using HATU (285 mg, 0.75 mmol, 5 equiv) and DIEA (261 mL, 1.5 mmol, 10 equiv) in DMF (2.5 mL). In all cases, after 90 min of coupling, the ninhydrin or chloranil (after incorporation of D-Val) tests were negative. Removal of Fmoc group and washings were carried out as described in General Procedures. An aliqout of the peptidyl-resin was treated with TFA-H$_2$O (9:1) for 60 min and the HPLC (Condition B, t$_R$ 17.2 min) of the crude obtained after evaporation showed a purity of >82%. ESMS, calcd for $C_{66}H_{116}N_{12}O_{17}$, 1,348.9. Found: m/z 1,350.0 [M+H]$^+$.

Example 4

5-MeHex-D-Val-Thr(tBu)-Val-D-Val-D-Pro-Orn(Boc)-D-allo-Ile-D-allo-Thr(Val-Thr-Phe-Alloc)-D-allo-Ile-D-Val-O-TrtCl-resin.

Alloc group was removed with Pd(PPh3)$_4$ (17.3 mg, 0.015 mmol, 0.1 equiv) in the presence of PhSiH$_3$ (185 μL, 1.5 mmol, 10 equiv) under atmosphere of Ar. Fmoc-Thr-OH (free hydroxy group) (256 mg, 0,75 mmol, 5 equiv) and Alloc-Phe-OH (187 mg, 0,75 mmol, 5 equiv) were added sequentially to the above peptidyl-resin (Example 3) using HATU (285 mg, 0.75 mmol, 5 equiv) and DIEA (261 mL, 1.5 mmol, 10 equiv) in DMF (2.5 mL). In all cases, after 90 min of coupling, the ninhydrin test was negative. Removal of Fmoc group and washings were carried out as described in General Procedures. An aliqout of the peptidyl-resin was treated with TFA-H$_2$O (9:1) for 60 min and the HPLC of the crude obtained after evaporation showed a purity by HPLC (Condition B, t$_R$ 17.8 min) of >70%. ESMS, calcd for $C_{79}H_{132}N_{14}O_{20}$, 1,597.0. Found: m/z 1,598.2 [M+H]$^+$.

Example 5

5-MeHex-D-Val-Thr(tBu)-Val-D-Val-D-Pro-Orn(Boc)-D-allo-Ile-D-allo-Thr(Val-Z-Dhb-Phe-H)-D-allo-Ile-D-Val-O-TrtCl-resin (via dehydration in solid-phase).

The above peptidyl-resin (Example 4) was treated with EDC (2.88 g, 15 mmol, 100 equiv), CuCl (891 mg, 9 mmol, 60 equiv) in CH$_2$Cl$_2$-DMF (10:2) (12 mL) for 6 days. After extensively washings with DMF, CH$_2$Cl$_2$, and DMF, the Alloc group was removed with Pd(PPh$_3$)$_4$ (17.3 mg, 0.015 mmol, 0.1 equiv) in the presence of PhSiH$_3$ (185 μL, 1.5 mmol, 10 equiv) under atmosphere of Ar. The final loading as calculated by AAA was 0.11 mmol/g (92% overall yield). An aliquot of the peptidyl-resin was treated with TFA-H$_2$O (9:1) for 60 min and the HPLC (Condition B, t$_R$ 17.2 min) of the crude obtained after evaporation showed a purity by of >70°/. ESMS, calcd for $C_{75}H_{126}N_{14}O_{17}$, 1495.0 Found: m/z 1,496.0 [M+H]$^+$.

Example 6

5-MeHex-D-Val-Thr(tBu)-Val-D-Val-D-Pro-Orn(Boc)-D-allo-Ile-D-allo-Thr(Val-Z-Dhb-Phe-H)-D-allo-Ile-D-Val-OH.

The protected peptide was cleaved from the resin (0.5 g, 55.9 μmol) by TFA-CH$_2$Cl$_2$ (1:99) (5×30 sec). The combined filtrates were evaporated to dryness under reduced pressure and lyophilized, to give 80.2 mg (48.5 μmol, 87% yield) of the title compound with a purity of >70% as checked by HPLC (Condition B, t$_R$ 25.7 min). ESMS, calcd for $C_{84}H_{142}N_{14}O_{19}$, 1,651.1. Found: m/z 1,652.3 [M+H]$^+$.

Example 7

Kahalalide F (I).

The protected peptide (Example 6) (40.0 mg, 24 μmol) was dissolved in DMF (25 mL), and PyBOP (37.8 mg, 73 μmol, 3 equiv) and DIEA (25 mL, 145 μmol, 6 equiv) were added. The mixture was allowed to stir for 1 h, and then the solvent was removed by evaporation under reduced pressure. The protected cyclic peptide was dissolved in TFA-H$_2$O (19:1, 5 mL) and the mixture was allowed to stir for 1 h. The solvent was removed by evaporation under reduced pressure, and then H$_2$O (5 mL) was added and lyophilized. The crude product was purified by medium pressure chromatography (Vydac C$_{18}$ 15-20 μm, 300 Å, 240×24 mm), linear gradient from 20% to 60% of acetonitrile (+0.05% TFA) in water (+0.05% TFA) in 5 h (300 mL each solvent), 120 mL/h, detection at 220 nm, to give the title product (5.0 mg, 3.4 μmol, 14% yield). MALDI-TOF-MS, calcd for $C_{75}H_{124}N_{14}O_{16}$, 1,477.9. Found: m/z 1,478.7 [M+H]$^+$, 1,500.6 [M+Na]$^+$, 1,516.5 [M+K]$^+$. The product co-eluted by HPLC [Condition D (t$_R$ 12.5 min), E (t$_R$ 17.4 min), and F(t$_R$ 12.1 min)] with an authentic sample of Kahalalide F. The $^1$H-NMR (500 MHz, d$^6$-DMSO) spectrum of the compound was identical to the natural product (data shown in Table I).

TABLE I

| RESIDUE | N—H | Hα | Hβ | OTHER |
|---|---|---|---|---|
| (Z)-Dhb | 9.69(s) | — | 6.34(q, J=7.0Hz) | 1.26(d, J=7.5Hz, γ-CH$_3$) |
| D-al•lo-Ile 1 | 8.82(d, J=10.0Hz) | 4.31 | 1.73 | 1.31, 1.02, 0.77(γ-CH$_2$, γ-CH$_3$, δ-CH$_3$) |
| L-Phe | 8.79(d, J=5.5Hz) | 4.42 | 2.93(m) | 7.20(1H Ar, m) 7.28(4H Ar, m) |

TABLE I-continued

| RESIDUE | N—H | Hα | Hβ | OTHER |
|---|---|---|---|---|
| D-al•lo-Thr | 8.56(d, J=8.0Hz) | 4.53 | 4.96(m) | 1.07(δ, J=6.5Hz, γ-$CH_3$) |
| D-Val 3 | 8.10(d, J=8.5Hz) | 4.26 | 1.94 | 0.86(2 γ-$CH_3$) |
| L-Orn | 7.95(d, J=8.5Hz) | 4.49 | 1.48(2H) | 1.67(γ-$CH_2$), 2.74(bs, δ-$CH_2$), 7.69(ε-$NH_3^+$) |
| D-al•lo-Ile 2 | 7.90(d) | 4.37 | 1.69 | 1.30, 1.03, 0.77(γ-$CH_2$, γ-$CH_3$, δ-$CH_3$) |
| D-Val 5 | 7.88(d) | 4.23 | 1.96 | 0.84(2 γ-$CH_3$) |
| L-Thr | 7.82(d, J=8.0Hz) | 4.26 | 3.97(m) | 4.88(d, J=5.0Hz, OH), 0.98(d, J=6.5Hz, γ-$CH_3$) |
| D-Val 2 | 7.62(d, J=8.5Hz) | 4.46 | 2.17 | 0.77(γ-$CH_3$), 0.62(d, J=7.0Hz, γ-$CH_3$) |
| L-Val 4 | 7.57(d, J=8.5Hz) | 4.28 | 1.98 | 0.80(2 γ-$CH_3$) |
| L-Val 1 | 6.76(d, J=9.0Hz) | 3.86 | 1.39 | 0.62(d, J=7.0Hz, γ-$CH_3$), 0.58(d, J=6.0Hz, γ-$CH_3$) |
| D-Pro | — | 4.36 | | 2.03, 1.87, 1.79(β-$CH_2$, γ-$CH_2$), 3.76(1H, m, δ-$CH_2$), 3.53(1H, m, —$CH_2$) |
| 5-MeHex | — | 2.13 (2H) | | 1.47(β-$CH_2$, δ-CH), 1.11(γ-$CH_2$), 0.82(2 ε-$CH_3$) |

Example 7bis

5-MeHex-D-Val-Thr-Val-D-Val-D-Pro-Orn-D-alloIle-cyclo (D-alloThr-D-allo-Ile-Val-Phe-ZDhb-Val).

Obtained as a side product during the preparation (racemization during the cyclization step) of Example 7. The product was characterized by HPLC ($t_R$ 17.4 min, Condition B) and ESMS, calcd for $C_{75}H_{124}N_{14}O_{16}$, 1,477.9. Found: m/z 1,501.3 [M+Na]$^+$, 1,517.3 [M+K]$^+$.

Kahalalide F (I)

Example 8

Alloc-Phe-Thr-OtBu.

H-Thr-OtBu-HCl (3.1 g, 15 mmol, 1.3 equiv) was dissolved in $CH_2Cl_2$ (30 mL) and DIEA (2.9 mL, 17 mmol, 1.5 equiv) was added and the mixture allowed to stir for 30 min. Alloc-Phe-OH (2.8 g, 11 mmol, 1 equiv) and EDC (2.8 g, 15 mmol, 1.3 equiv) in $CH_2Cl_2$ (35 mL) was then added and the reaction was stirred for 18 h. The organic reaction mixture was washed with $H_2O$ (3×25 mL), dried ($MgSO_4$) and concentrated in vacuo. The resultant oil (4.12 g) was purified by flash chromatography [$CHCl_3$-MeOH—HOAc (9:1:0.2)] to give the title product (3.25 g, 8 mmol, 71% yield), which was characterized by analytical HPLC ($t_R$ 20.9 min, >98% purity; Condition C); ESMS, calcd for $C_{21}H_{30}N_2O_6$, 406.2. Found: m/z 408.0 [M+H]$^+$; $^1$H-NMR (200 MHz, $CDCl_3$): 7.1-7.3 (5H, m, Ar); 6.89 (1H, d, J=8.8 Hz, NH); 5.7-5.9 (1H, m, CH allyl); 5.56 (1H, d, J=8.0 Hz, OH); 5.2-5.3 (2H, m, $CH_2$ g-allyl); 4.52 (2H, d, J=5.4 Hz, $CH_2$ a-allyl); 4.45 (1H, dd, J=8.4 Hz, 2.8 Hz, a-CH Thr); 4.22 (1H, dq, J=6.2 Hz, J=3.0 Hz, b-CH Thr); 3.0-3.2 (2H, m, b-$CH_2$ Phe); 1.47 (9H, s, tBu); 1.15 (3H, d, J=6.6 Hz, g-$CH_3$ Thr); $^{13}$C-NMR (50 MHz, $CDCl_3$): 172.2 (CO), 169.5 (CO); 156.0 (CO); 136.1 (Cq, Ar); 132.5 (CH, allyl); 129.3 (CH, Ar); 128.5 (CH, Ar); 126.9 (CH, Ar); 117.7 ($CH_2$, allyl); 82.7 (Cq, tBu); 68.5 (b-CH Thr); 65.9 ($CH_2$, allyl); 58.0 (a-CH Thr); 56.2 (a-CH Phe); 38.3 (b-$CH_2$ Phe); 28.0 ($CH_3$, tBu); 20.8 (g-$CH_3$ Thr).

Example 9

Alloc-Phe-ZDhb-OtBu.

Alloc-Phe-Thr-OtBu (3.25 g, 8.0 mmol), EDC (9.90 g, 52 mmol, 6.5 equiv), and CuCl (2.14 g, 22 mmol, 2.7 equiv) were dissolved in $CH_2Cl_2$-anhydrous DMF (65 ml, 12:1) under $N_2$ and the mixture was allowed to stir for 2 days under $N_2$. The organic solvent was removed in vacuo and the residue was taken in a saturated solution of EDTA (100 mL), which was extracted with EtOAc (3×50 mL). The combined organic solution was washed with brine (3×60 mL) dried ($MgSO_4$) and concentrated in vacuo to give a pale yellow solid (2.8 g), was purified by flash chromatography [$CHCl_3$-MeOH—HOAc (9:1:0.1)] to give the title product (2.6 g, 6.7 mmol, 84°/yield), which was characterized by analytical HPLC ($t_R$ 23.1 min, >95% purity; Condition C); ESMS, calcd for $C_{21}H_{28}N_2O_5$, 388.2. Found: m/z 389.6 [M+H]$^+$; $^1$H-NMR (200 MHz, $CDCl_3$): 7.2-7.4 (5H, m, Ar); 6.69 (1H, q, J=7.4 Hz, CH Dhb); 5.8-6.0 (1H, m, CH allyl); 5.2-5.3 (2H, m, $CH_2$ g-allyl); 4.5-4.6 (2H, m, a-$CH_2$ allyl); 3.1-3.3 (2H, m, b-$CH_2$ Phe); 1.67 (3H, d, J=7.2 Hz, $CH_3$ Dhb); 1.47 (9H, s, tBu); $^{13}$C-NMR (50 MHz, $CDCl_3$): 168.9 (CO); 163.1 (CO); 156.0 (CO); 136.0 (Cq, Ar); 132.6, 132.3 (CH, allyl; b-CH Dhb); 129.3 (CH, Ar); 128.7 (CH, Ar); 127.0 (CH, Ar); 117.9 ($CH_2$, allyl); 81.7 (Cq, tBu); 66.0 ($CH_2$, allyl); 56.3 (a-CH Phe); 38.2 (b-$CH_2$ Phe); 28.0 ($CH_3$, tBu); 14.7 ($CH_3$ Dhb).

Example 10

Alloc-Phe-ZDhb-OH.

Alloc-Phe-ZDhb-OtBu (2.6 g, 6.7 mmol) was dissolved in TFA-$CH_2Cl_2$—$H_2O$ (90:8:2, 5.5 mL) and the mixture was allowed to stir for 3 h. The organic reaction was concentrated in vacuo to give the title product (2.2 g, 6.6 mmol, 99% yield), which was characterized by analytical HPLC ($t_R$ 17.0 min, >95% purity; Condition C); ESMS, calcd for $C_{17}H_{20}N_2O_5$, 332.1. Found: m/z 333.7 [M+H]$^+$; $^1$H-NMR (200 MHz, CD$_3$OD): 7.2-7.3 (5H, m, Ar); 6.84 (1H, q, J=7.2 Hz, CH Dhb); 5.8-6.0 (1H, m, CH allyl); 5.1-5.3 (2H, m, CH$_2$ g-allyl); 4.4-4.5 (2H, m, a-CH$_2$ allyl); 3.2-3.3 (1H, m, b-CH$_2$ Phe); 2.8-3.0 (1H, m, b-CH$_2$ Phe); 1.66 (3H, d, J=7.4 Hz, CH$_3$ Dhb); $^{13}$C-NMR (50 MHz, CD$_3$OD): 173.1 (CO); 138.5 (Cq, Ar); 136.7, 134.1 (CH, allyl; b-CH Dhb); 130.3 (CH, Ar); 129.4 (CH, Ar); 127.7 (CH, Ar); 117.4 (CH$_2$, allyl); 66.6 (CH$_2$, allyl); 57.8 (a-CH Phe); 39.1 (b-CH$_2$ Phe); 14.1 (CH$_3$ Dhb).

Example 11

5-MeHex-D-Val-Thr(tBu)-Val-D-Val-D-Pro-Orn(Boc)-D-allo-Ile-D-allo-Thr(Val-Alloc)-D-allo-Ile-D-Val-O-TrtCl-resin.

Cl-TrtCl-resin (0.45 g, 1.35 mmol/g) was placed in a 10 mL polypropylene syringe fitted with a polyethylene filter disk. The peptidyl-resin was obtained following the same procedure described in Examples 1-3 except that in the coupling of the first aminoacid (Fmoc-D-Val-OH) to the resin 0.3 equiv instead of 0.2 equiv were used. The initial loading as calculated by AAA was 0.29 mmol/g. Once the aminoacids were coupled, an aliquot of the peptidyl-resin was treated with TFA-H$_2$O (9:1) for 60 min and the HPLC (Condition B, $t_R$ 17.3 min) of the crude obtained after evaporation showed a purity of >80%. ESMS, calcd for C$_{66}$H$_{116}$N$_{12}$O$_{17}$, 1,348.9. Found: m/z 1,350.1 [M+H]$^+$.

Example 12

5-MeHex-D-Val-Thr(tBu)-Val-D-Val-D-Pro-Orn(Boc)-D-allo-Ile-D-allo-Thr(Val-ZDhb-Phe-Alloc)-D-allo-Ile-D-Val-O-TrtCl-resin (via incorporation of the dipeptide).

The peptidyl-resin was treated with Pd(PPh3)$_4$ (15.1 mg, 0.013 mmol, 0.1 equiv) in the presence of PhSiH3 (161 µL, 1.3 mmol, 10 equiv) under atmosphere of Ar, for removing the Alloc group. Alloc-Phe-ZDhb-OH (217 mg, 0.65 mmol, 5 equiv) and HATU (249 mg, 0.65 mmol, 5 equiv) were dissolved in DMF (1.25 mL) and added to peptidyl-resin, then DIEA (228 µL, 1.3 mmol, 10 equiv) was added and the mixture stirred overnight. After washings, the coupling was repeated with the same amount of reagents for 3 h., when the ninhydrin test was negative. After washings with DMF and CH$_2$Cl$_2$, an aliquot of the peptidyl-resin was treated with TFA-H$_2$O (9:1) for 60 min and the HPLC (Condition B, $t_R$ 18.3 min) of the crude obtained after evaporation showed a purity by of >80%. MALDI-TOF-MS, calcd for C$_{79}$H$_{130}$N$_{14}$O$_{19}$, 1,579.0. Found: m/z 1,580.3 [M+H]$^+$, 1,602.2 [M+Na]$^+$, 1,618.2 [M+K]$^+$.

Example 13

5-MeHex-D-Val-Thr(tBu)-Val-D-Val-D-Pro-Orn(Boc)-D-allo-Ile-D-allo-Thr(Val-ZDhb-Phe-H)-D-allo-Ile-D-Val-OH.

The Alloc group from peptidyl-resin (Example 12) was removed with Pd(PPh3)$_4$ (15.1 mg, 0.013 mmol, 0.1 equiv) in the presence of PhSiH3 (161 µL, 1.3 mmol, 10 equiv) under atmosphere of Ar. The final loading as calculated by AAA was 0.16 mmol/g (79% overall yield). The protected peptide was cleaved from the resin (235 mg, 37.5 mmol) by TFA-CH$_2$Cl$_2$ (1:99) (5×30 sec). The combined filtrates were evaporated to dryness under reduced pressure and lyophilized, to give 40.5 mg (24.5 mmol, 65%) of the title compound with a purity >80% as checked by HPLC (Condition B, $t_R$ 24.3 min). MALDI-TOF-MS, calcd for C$_{84}$H$_{142}$N$_{14}$O$_{19}$, 1,651.1. Found: m/z 1,674.8 [M+Na]$^+$, 1,690.8 [M+K]$^+$.

Example 14

Kahalalide F (I).

The protected peptide (Example 13) (38.5 mg, 23 µmol) was dissolved in DMF (25 mL), and PyBOP (36.4 mg, 70 µmol, 3 equiv) and DIEA (24 mL, 140 µmol, 6 equiv) were added. The mixture was allowed to stirr for 1 h, and then the solvent was removed by evaporation under reduced pressure. The protected cyclic peptide was dissolved in TFA-H$_2$O (19:1, 5 mL) and the mixture was allowed to stir for 1 h. The solvent was removed by evaporation under reduced pressure, and then H$_2$O (5 mL) was added and lyophilized. The crude product was purified as described in Example 7 to give the title product (3.6 mg, 2.4 µmol, 10% yield), which was identical to the one obtained in Example 7.

5-MeHex-D-Val-Thr-D-Val-Val-D-Pro-Orn-D-allo-Ile-cyclo(D-allo-Thr-D-allo-Ile-D-Val-Phe-ZDhb-Val) (structure assigned to Kahalalide F by Goetz, G., et al. *Tetrahedron*, 1999, vol. 55, pp. 7739-7746)

Example 15

5-MeHex-D-Val-Thr-D-Val-Val-D-Pro-Orn-D-allo-Ile-cyclo(D-allo-Thr-D-allo-Ile-D-Val-Phe-ZDhb-Val) (via dehydration in solid-phase).

Experimental procedures as decribed in Examples 1-7 were carried out with the only exception that, in Example 3, Fmoc-Val-OH was incorporated to D-Pro-peptidyl-resin and then after removal of the Fmoc group, the Fmoc-D-Val-OH was incorporated. The final loading as calculated by AAA was 0.106 mmo/g (87% overall yield), the cleavage yield was of the 83%, and 4.7 mg of the title compound were obtained, which represented a 13% overall yield in cyclization, deprotection and purification steps. This product eluted in HPLC 0.8-1.9 min later than an authentic sample of Kahalalide F [Condition D ($t_R$ 13.3 us 12.5 min), E ($t_R$ 18.8 us 17.4 min), and F($t_R$ 14.0 vs 12.1 min)]. MALDI-TOF-MS, calcd for C$_{75}$H$_{124}$N$_{14}$O$_{16}$, 1,477.9. Found: m/z 1,478.7 [M+H]$^+$, 1,500.7 [M+Na]$^+$, 1,516.6 [M+K]$^+$.

The $^1$H-NMR (500 MHz, d$^6$-DMSO) spectrum of the compound (Tables II and III) was different from the one obtained for an authentic sample of Kahalalide F. The greatest difference was that the synthetic compound obtained, showed two conformations dued to a cis-trans equilibrium between L-Val-D-Pro residues which was not observed neither in the natural product nor in the isomer obtained in example 7.

TABLE II

| (Major, trans isomer) | | | | |
|---|---|---|---|---|
| RESIDUE | N—H | Hα | Hβ | OTHER |
| (Z)-Dhb | 9.67(s) | — | 6.33(q) | 1.27(d, J=7.0Hz, γ-CH$_3$) |
| D-al•lo-Ile 1 | 8.80(d) | 4.31 | 1.73 | 1.32, 0.77(γ-CH$_2$, γ-CH$_3$, δ-CH$_3$) |
| L-Phe | 8.78(d, J=5.5Hz) | 4.43 | 2.93(m) | 7.20(1H Ar, m) 7.28(4H Ar, m) |
| D-al•lo-Thr | 8.58(d, J=9.0Hz) | 4.53 | 4.95(m) | 1.07(d, J=6.5Hz, γ-CH$_3$) |
| L-Val 3 | 7.97(d, J=8.0Hz) | 4.34 | 1.94 | 0.84(2 γ-CH$_3$) |
| L-Orn | 7.77(d, J=8.5Hz) | 4.47 | 1.46(2H) | 1.66(γ-CH$_2$), 2.72(bs, δ-CH$_2$), 7.66(ε-NH$_3^+$) |

TABLE II-continued (Major, trans isomer)

| RESIDUE | N—H | Hα | Hβ | OTHER |
|---|---|---|---|---|
| D-al•lo-Ile 2 | 7.87(d, J=8.5Hz) | 4.37 | 1.68 | 0.75(δ-CH$_3$ o d-CH$_3$ and γ-CH$_3$) |
| D-Val 5 | 7.90 | 4.22 | 1.95 | 0.85(2 γ-CH$_3$) |
| L-Thr | 7.90(d) | 4.24 | 4.02 | 4.98(OH), 1.02(γ-CH$_3$) |
| D-Val 2 | 7.63(d, J=8.5Hz) | 4.45 | 2.18 | 0.77(γ-CH$_3$), 0.62 (γ-CH$_3$) |
| D-Val 4 | 7.56(d, J=9.0Hz) | 4.34 | 2.02 | 0.84(γ-CH$_3$), 0.79 (γ-CH$_3$), |
| L-Val 1 | 6.75(d) | 3.86 | 1.39 | 0.62(2 γ-CH$_3$) |
| D-Pro | — | 4.30 | | 2.03, 1.81, 1.73(β-CH$_2$, γ-CH$_2$), 3.73(1H, m, δ-CH$_2$), 3.52(1H, m, δ-CH$_2$) |
| 5-MeHex | — | 2.08 (1H) 2.15 (1H) | | 1.48(b-CH$_2$, δ-CH), 1.11(γ-CH$_2$), 0.82(2 ε-CH$_3$) |

TABLE III (Minor, cis isomer)

| RESIDUE | N—H | Hα | Hβ | OTHER |
|---|---|---|---|---|
| (Z)-Dhb | 9.63(s) | — | 6.33(q) | 1.28(d, J=6.5Hz, γ-CH$_3$) |
| D-al•lo-Ile 1 | 8.76(d) | 4.30 | 1.71 | 1.33, 0.76(γ-CH$_2$, γ-CH$_3$, δ-CH$_3$) |
| L-Phe | 8.78(d, J=5.5Hz) | 4.43 | 2.93(m) | 7.20(1 H Ar, m) 7.28(4H Ar, m) |
| D-al•lo-Thr | 8.58(d, J=9.0Hz) | 4.53 | 4.95(m) | 1.00(γ-CH$_3$) |
| L-Val 3 | 8.06(d, J=8.5Hz) | 4.11 | 1.81 | 0.71(γ-CH$_3$), 0.60(γ-CH$_3$) |
| L-Orn | 8.37(d, J=9.0Hz) | 4.62 | 1.52(2H) | 1.64(γ-CH$_2$), 2.78(bs, δ-CH$_2$), 7.66(ε-NH$_3$⁺) |
| D-al•lo-Ile 2 | 8.09(d, J=9.0Hz) | 4.42 | 1.64 | 0.77(δ-CH$_3$ or d-CH$_3$ and γ-CH$_3$) |
| D-Val 5 | 7.90 | 4.22 | 1.95 | 0.85(2 γ-CH$_3$) |
| L-Thr | 7.88(d) | 4.23 | 3.99 | 4.93(OH), 1.02(γ-CH$_3$) |
| D-Val 2 | 7.63(d, J=8.5Hz) | 4.45 | 2.18 | 0.77(γ-CH$_3$), 0.62(γ-CH$_3$) |
| D-Val 4 | 7.49(d, J=9.0Hz) | 4.34 | 1.94 | 0.79(γ-CH$_3$), 0.73(γ-CH$_3$), |
| L-Val 1 | 6.72(d) | 3.84 | 1.38 | 0.62(2 γ-CH$_3$) |
| D-Pro | — | 4.93 | | 2.06, 1.89, 1.75(β-CH$_2$, γ-CH$_2$), 3.3(m, δ-CH$_2$) |
| 5-MeHex | — | 2.08 (1H) 2.15 (1H) | | 1.48(β-CH$_2$, δ-CH), 1.11(γ-CH$_2$), 0.82(2 ε-CH$_3$) |

Example 15bis

5-MeHex-D-Val-Thr-D-Val-Val-D-Pro-Orn-D-allo-Ile-cyclo(D-allo-Thr-D-allo-Ile-Val-Phe-ZDhb-Val).

Obtained as a side product during the preparation (racemization during the cyclization step) of Example 15. The product was characterized by HPLC ($t_R$ 17.6 min, Condition B) and MALDI-TOF-MS, calcd for $C_{75}H_{124}N_{14}O_{16}$, 1,477.9. Found: m/z 1,479.3 [M+H]⁺, 1,501.2 [M+Na]⁺, 1,517.2 [M+K]⁺.

Example 16

5-MeHex-D-Val-Thr-D-Val-Val-D-Pro-Orn-D-allo-Ile-cyclo(D-allo-Thr-D-allo-Ile-D-Val-Phe-ZDhb-Val) (uia incorporation of the dipeptide).

Experimental procedures as described in Examples 8-14 were carried out with the only exception that, as in Example 14, Fmoc-Val-OH was incorporated to D-Pro-peptidyl-resin and then after removal of the Fmoc group, the Fmoc-D-Val-OH was incorporated. The final loading as calculated by AAA was 0.16 mmol/g (79% overall yield), the cleavage yield was of the 78%, and 3.4 mg of the title compound were obtained, which represented a 10% overall yield in cyclization, deprotection and purification steps. The product purified was identical to the one obtained in Example 15.

Hamann et al. Kahalalide B [5-MeHex-Tyr-cyclo(D-Ser-Phe-D-Leu-Pro-Thr-Gly)]

Example 17

H-Thr(tBu)-O-TrtCl-resin.

Cl-TrtCl-resin (0.5 g, 1.35 mmol/g) was placed in a 10 mL polypropylene syringe fitted with a polyethylene filter disk. The resin was then washed with CH$_2$Cl$_2$ (5×0.5 min), and a solution of Fmoc-Thr(tBu)-OH (54 mg, 0.135 mmol, 0.2 equiv) and DIEA (235 mL, 1.35 mmol, 2 equiv) in CH$_2$Cl$_2$ (1.25 mL) was added, and the mixture was stirred for 1 h. The reaction was terminated by addition of MeOH (400 mL), after a stirring of 15 min. The Fmoc-Thr(tBu)-O-TrtCl-resin was subjected to the following washings/treatments with CH$_2$Cl$_2$ (3×0.5 min), DMF (3×0.5 min), piperidine-CH$_2$Cl$_2$-DMF (1:9.5:9.5, 1×10 min), piperidine-DMF (1:4, 1×15 min), DMF (5×0.5 min), isopropanol (2×1 min), DMF (5×0.5 min), MeOH (2×1 min), and dried over vacuum. The loading as calculated by AAA was 0.15 mmol/g.

Example 18

5-MeHex-Tyr-D-Ser(Gly-H)-Phe-D-Leu-Pro-Thr-OH.

Fmoc-Pro-OH (178 mg, 0.53 mmol, 7 equiv), Fmoc-D-Leu-OH (187 mg, 0.53 mmol, 7 equiv), Fmoc-Phe-OH (204 mg, 0.53 mmol, 7 equiv), Fmoc-D-Ser-OH (free hydroxy group) (173 mg, 0.53 mmol, 7 equiv), Fmoc-Tyr(tBu)-OH (243 mg, 0.53 mmol, 7 equiv), and 5-MeHex-OH (69 mg, 0.53 mmol, 7 equiv) were added sequentially to the above obtained H-Thr(tBu)-O-TrtCl-resin using DIPCDI (82 µL, 0.53 mmol, 7 equiv) and HOBt (81 mg, 0.53 mmol, 7 equiv) in DMF (1.25 mL). In all cases except for D-Ser, after 90 min of coupling, the ninhydrin test was negative. Fmoc-DSer-OH (173 mg, 0.53 mmol, 7 equiv) was recoupled with HATU (201 mg, 0.53 mmol, 7 equiv) in the presence of DIEA (184 µL, 1.06 mmol, 14 equiv) in DMF for 90 min. Removal of Fmoc group and washings were carried out as described in General Procedures. Boc-Gly-OH (119 mg, 0.68 mmol, 9 equiv) was coupled with DIPCDI (105 µL, 0.68 mmol, 9 equiv) in the presence of DMAP (8.3 mg, 68 µmol, 0.9 equiv) for 2.5 h. The coupling was repeated with fresh reagents for 1.5 h. The final loading was 0.10 mmol/g, which represented a 77% synthesis yield. The unprotected peptide was cleaved from the resin (525 mg, 54 µmol) by TFA-H$_2$O (92:8) for 2 h. The combined filtrates were evaporated to dryness under reduced pressure, H₂O (5 mL) was added, and the solution lyophilized to give 43.0 mg (48.0 μmol, 89% yield) of the title compound with a purity of >85% as checked by HPLC (Condition A, $t_R$ 18.5 min). ESMS, calcd for $C_{45}H_{65}N_7O_{12}$, 895.5. Found: m/z 896.6 [M+H]⁺.

Example 19

Kahalalide B [5-MeHex-Tyr-cyclo(D-Ser-Phe-D-Leu-Pro-Thr-Gly)].

The unprotected peptide (Example 18) (40.5 mg, 45 μmol) was dissolved in DMF (48 mL), and PyBOP (70 mg, 0.135 mmol, 3 equiv) and DIEA (47 mL, 0.271 mmol, 6 equiv) were added. The mixture was allowed to stirr for 2 h, and then the solvent was removed by evaporation under reduced pressure, H₂O (5 mL) was added, and the solution lyophilized. The crude product was purified by medium pressure chromatography (Vydac $C_{18}$ 15-20 μm, 300 Å, 240×24 mm), linear gradient from 20% to 60% of acetonitrile (+0.05% TFA) in water (+0.05% TFA) in 5 h (300 mL each solvent), 120 mL/h, detection at 220 nm, to give the title product (8.7 mg, 9.9 μmol, 22% yield). The product was characterized by HPLC (Condition A, $t_R$ 21.6 min) and MALDI-TOF-MS, calcd for $C_{45}H_{63}N_7O_{11}$, 877.5. Found: m/z 878.7 [M+H]⁺, 900.6 [M+Na]⁺, 916.5 [M+K]⁺. AAA: Gly 1.02 (1), Thr 0.95 (1), Phe 0.99 (1), Ser 1.00 (1), Pro 1.20 (1), Leu 1.00 (1), Tyr 0.87 (1).

Example 20

5-MeHex-D-Val-Thr-Val-D-Val-D-Pro-Orn-D-allo-Ile-cyclo(D-allo-Thr-D-allo-Ile-D-Val-Phe-Etg-Val).

Experimental procedures as decribed in Examples 1-4 and 6-7, starting with 200 mg of resin, were carried out with the only exception that, in Example 4, Fmoc-Thr-OH was replaced by Fmoc-Etg-OH. The product was characterized by HPLC ($t_R$ 16.8 min, Condition B) and MALDI-TOF-MS, calcd for $C_{75}H_{126}N_{14}O_{16}$, 1,479.0. Found: m/z 1,480.2 [M+H]⁺, 1,502.2 [M+Na]⁺, 1,518.0 [M+K]⁺.

Example 20b

5-MeHex-D-Val-Thr-Val-D-Val-D-Pro-Orn-D-allo-Ile-cyclo(D-allo-Thr-D-allo-Ile-D-Val-Phe-D-Etg-Val).

Experimental procedures as decribed in Examples 1-4 and 6-7, starting with 200 mg of resin, were carried out with the only exception that, in Example 4, Fmoc-Thr-OH was replaced by Fmoc-D-Etg-OH. The product was characterized by HPLC ($t_R$ 17.0 min, Condition B) and MALDI-TOF-MS, calcd for $C_{75}H_{126}N_{14}O_{16}$, 1,479.0. Found: m/z 1,501.0 [M+Na]⁺, 1,517.9 [M+K]⁺.

Example 20c

5-MeHex-D-Val-Thr-Val-D-Val-D-Pro-Orn-D-alloIle-yclo(D-allo-Thr-D-allo-Ile-D-Val-Phe-D-Thr-Val).

Experimental procedures as decribed in Examples 1-4 and 6-7, starting with 200 mg of resin, were carried out with the only exception that, in Example 4, Fmoc-Thr(tBu)-OH was replaced by Fmoc-D-Thr(tBu)-OH. The product was characterized by HPLC ($t_R$ 19.9 min, Condition B) and MALDI-TOF-MS, calcd for $C_{75}H_{126}N_{14}O_{17}$, 1,494.9. Found: m/z 1,517.4 [M+Na]⁺, 1,533.4 [M+K]⁺.

Example 20d

5-MeHex-D-Val-Thr-Val-D-Val-D-Pro-Orn-D-allo-Ile-cyclo(D-allo-Thr-D-allo-Ile-D-Val-Phe-D-allo-Thr-Val).

Experimental procedures as decribed in Examples 1-4 and 6-7, starting with 200 mg of resin, were carried out with the only exception that, in Example 4, Fmoc-Thr(tBu)-OH was replaced by Fmoc-D-alloThr-OH. The product was characterized by HPLC ($t_R$ 18.0 min, Condition B) and MALDI-TOF-MS, calcd for $C_{75}H_{126}N_{14}O_{17}$, 1,494.9. Found: m/z 1,496.6 [M+H]⁺, 1,518.6 [M+Na]⁺, 1,534.6 [M+K]⁺.

Example 20e

5-MeHex-D-Val-Thr-Val-D-Val-D-Pro-Orn-D-allo-Ile-cyclo(D-allo-Thr-D-allo-Ile-D-Val-Phe-D-Phe-Val).

Experimental procedures as decribed in Examples 1-7, starting with 200 mg of resin, were carried out with the only exception that, in Example 4, Fmoc-Thr-OH was replaced by Fmoc-D/L-(b-OH)Phe-OH. The product was characterized by HPLC ($t_R$ 22.2 min, Condition B) and MALDI-TOF-MS, calcd for $C_{80}H_{126}N_{14}O_{16}$, 1,538.95. Found: m/z 1,540.3 [M+H]⁺, 1,562.4 [M+Na]⁺, 1,578.3 [M+K]⁺.

Example 21

5-MeHex-D-Val-Thr-Val-D-Val-D-Pro-Orn-D-allo-Ile-cyclo(D-Dpa-D-allo-Ile-D-Val-Phe-ZDhb-Val).

Experimental procedures as decribed in Examples 1-7, starting with 200 mg of resin, were carried out with the only exceptions that, in Example 2, Fmoc-D-allo-Thr-OH was replaced by Fmoc-D-Dpa(Alloc)-OH and that before the incorporation of Alloc-Val-OH, which was incorporated as the rest of protected amino acids, the Alloc group from the Dpa was removed as indicated above. The product was characterized by HPLC and ESMS, calcd for $C_{74}H_{123}N15O_{15}$, 1,461.9. Found: m/z 1,463.3 [M+H]⁺.

Example 22

But-D-Val-Thr-Val-D-Val-D-Pro-Orn-D-allo-Ile-cydo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by But-OH. The product was characterized by HPLC ($t_R$ 14.7 min, Condition B) and MALDI-TOF-MS, calcd for $C_{72}H_{118}N14O_{16}$, 1,435.9. Found: m/z 1,459.6 [M+Na]⁺, 1,475.6 [M+K]⁺.

Example 22bis

But-D-Val-Thr-Val-D-Val-D-Pro-Orn-D-allo-Ile-cyclo(D-allo-Thr-D-allo-Ile-Val-Phe-ZDhb-Val).

Obtained as a side product during the preparation (racemization during the cyclization step) of Example 22. The product was characterized by HPLC ($t_R$ 16.0 min, Condition B) and MALDI-TOF-MS, calcd for $C_{72}H_{118}N14O_{16}$, 1,435.9. Found: m/z 1,459.5 [M+Na]⁺, 1,475.5 [M+K]⁺.

Example 23

3-MeBut-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by 3-MeBut-OH. The product was characterized by HPLC ($t_R$ 15.9 min, Condition B) and MALDI-TOF-MS, calcd for $C_{73}H_{120}N_{14}O_{16}$, 1,449.9. Found: m/z 1,473.2 $[M+Na]^+$, 1,489.2 $[M+K]^+$.

Example 23bis

3-MeBut-D-Val-Thr-Val-D-Val-D-Pro-Orn-D-allo-Ile-cyclo(D-allo-Thr-D-allo-Ile-Val-Phe-Z-Dhb-Val).

Obtained as a side product during the preparation (racemization during the cyclization step) of Example 23. The product was characterized by HPLC ($t_R$ 17.0 min, Condition B) and ESMS, calcd for $C_{73}H_{120}N_{14}O_{16}$, 1,449.9. Found: m/z 1,473.3 $[M+Na]^+$, 1,489.4 $[M+K]^+$.

Example 24

3,3-DiMeBut-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by 3,3-DiMeBut-OH. The product was characterized by HPLC ($t_R$ 16.3 min, Condition B) and MALDI-TOF-MS, calcd for $C_{74}H_{122}N_{14}O_{16}$, 1,463.9. Found: m/z 1,487.4 [M+Na]+, 1,503.6 $[M+K]^+$.

Example 24bis 3,3-DiMeBut-D-Val-Thr-Val-D-Val-D-Pro-Orn-D-allo-Ile-cyclo(D-allo-Thr-D-allo-Ile-Val-Phe-ZDhb-Val).

Obtained as a side product during the preparation (racemization during the cyclization step) of Example 24. The product was characterized by HPLC ($t_R$ 17.6 min, Condition B) and MALDI-TOF-MS, calcd for $C_{74}H_{122}N_{14}O_{16}$, 1,463.9. Found: m/z 1,487.3 $[M+Na]^+$, 1,503.3 $[M+K]^+$.

Example 25

4-MePen-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by 4-MePen-OH. The product was characterized by HPLC ($t_R$ 16.5 min, Condition B) and MALDI-TOF-MS, calcd for $C_{74}H_{122}N_{14}O_{16}$, 1,463.9. Found: m/z 1,487.7 $[M+Na]^+$, 1,503.6 $[M+K]^+$.

Example 25bis

4-MePen-D-Val-Thr-Val-D-Val-D-Pro-Orn-D-allo-Ile-cyclo(β-allo-Thr-D-allo-Ile-Val-Phe-ZDhb-Val).

Obtained as a side product during the preparation (racemization during the cyclization step) of Example 25. The product was characterized by HPLC ($t_R$ 17.8 min, Condition B) and MALDI-TOF-MS, calcd for $C_{74}H_{122}N_{14}O_{16}$, 1,463-9. Found: m/z 1,487.8 $[M+Na]^+$, 1,503.6 $[M+K]^+$.

Example 26

Hep-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by Hep-OH. The product was characterized by HPLC ($t_R$ 17.5 min, Condition B) and MALDI-TOF-MS, calcd for $C_{75}H_{124}N_{14}O_{16}$, 1,477.9. Found: m/z 1,501.4 $[M+Na]^+$, 1,517.5 $[M+K]^+$.

Example 26bis

Hep-D-Val-Thr-Val-D-Val-D-Pro-Orn-D-allo-Ile-cyclo(D-allo-Thr-D-allo-Ile-Val-Phe-ZDhb-Val).

Obtained as a side product during the preparation (racemization during the cyclization step) of Example 26. The product was characterized by HPLC ($t_R$ 18.9 min, Condition B) and MALDI-TOF-MS, calcd for $C_{75}H_{124}N_{14}O_{16}$, 1,477-9. Found: m/z 1,501.6 $[M+Na]^+$, 1,517.7 $[M+K]^+$.

Example 27

Pal-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by Pal-OH. The product was characterized by HPLC ($t_R$ 22.1 min, Condition G) and MALDI-TOF-MS, calcd for $C_{84}H_{142}N_{14}O_{16}$, 1,603.1. Found: m/z 1,626.9 $[M+Na]^+$, 1,642.9 $[M+K]^+$.

Example 27bis

Pal-D-Val-Thr-Val-D-Val-D-Pro-Orn-D-allo-Ile-cyclo(D-allo-Thr-D-allo-Ile-Val-Phe-ZDhb-Val).

Obtained as a side product during the preparation (racemization during the cyclization step) of Example 27. The product was characterized by HPLC ($t_R$ 23.2 min, Condition G) and MALDI-TOF-MS, calcd for $C_{84}H_{142}N_{14}O_{16}$, 1,603.1. Found: m/z 1,626.8 $[M+Na]^+$, 1,642.8 $[M+K]^+$.

Example 27a

4-DiMeABut-D-Val-Thr-Val-D-Val-D-Pro-Orn-D-allo-Ile-cyclo(D-allo-Thr-D-allo-Ile-D-Val-Phe-Z-Dhb-Val).

Experimental procedures as decribed in Examples 1-7, starting with 200 mg of resin, were carried out with the only exceptions that, in Example 3, 5-MeHex was replaced by 4-DiMeABut-OH. The product was characterized by HPLC ($t_R$ 12.0 min, Condition B) and MALDI-TOF-MS, calcd for $C_{74}H_{123}N15O_{16}$, 1,477.9. Found: m/z 1,478.6 $[M+H]^+$, 1,500.6 $[M+Na]^+$, 1,516.6 $[M+K]^+$.

Example 27b

2-Hedo-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by 2-Hedo-OH. The product was characterized by HPLC ($t_R$ 15.8 min, Condition B) and MALDI-TOF-MS, calcd for $C_{74}H_{118}N_{14}O_{16}$, 1,458.9. Found: m/z 1,460.0 $[M+H]^+$, 1,482.0 $[M+Na]^+$, 1,497.9 $[M+K]^+$.

Example 27c

4-AcBut-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by 4-AcBut-OH. The product was characterized by HPLC ($t_R$ 18.2 min, Condition B) and MALDI-TOF-MS, calcd for $C_{74}H_{120}N_{14}O_{18}$, 1,492.9. Found: m/z 1,493.7 $[M+H]^+$, 1,515.8 [M+Na]+, 1,531.7 $[M+K]^+$.

Example 27d

4-HOBut-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by 4-HOBut-OH. The product was characterized by HPLC ($t_R$ 16.6 min, Condition B) and MALDI-TOF-MS, calcd for $C_{72}H_{118}N_{14}O_{17}$, 1,450.9. Found: m/z 1,451.6 $[M+H]^+$, 1,473.6 $[M+Na]^+$, 1,489.6 $[M+K]^+$.

Example 27e

Ac-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by HOAc. The product was characterized by HPLC ($t_R$ 17.0 min, Condition B) and MALDI-TOF-MS, calcd for $C_{70}H_{114}N_{14}O_{16}$, 1,406.9. Found: m/z 1,407.8 $[M+H]^+$, 1,429.8 $[M+Na]^+$.

Example 27f

TFA-D-Val-Thr-Val-D-Val-D-Pro-Orn-D-allo-Ile-cyclo(D-allo-Thr-D-allo-Ile-D-Val-Phe-ZDhb-Val).

Obtained as a side product during the preparation (trifluoroacetylion during the cyclization step) of Example 27e. The product was characterized by HPLC ($t_R$ 14.7 min, Condition B) and MALDI-TOF-MS, calcd for $C_{70}H_{111}F_3N_{14}O_{16}$, 1,460.8. Found: m/z 1,462.0 $[M+H]^+$, 1,484.1 $[M+Na]^+$, 1,500.0 $[M+K]^+$.

Example 27g

AcButBut-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by AcButBut-OH. The product was characterized by HPLC ($t_R$ 14.1 min, Condition B) and MALDI-TOF-MS, calcd for $C_{78}H_{126}N_{14}O_{20}$, 1,578.9. Found: m/z 1,581.2 $[M+H]^+$, 1,602.2 $[M+Na]^+$, 1,618.2 $[M+K]^+$.

Example 27h

IBut-D-allo-Ile-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by Fmoc-D-allo-Ile-OH, removal of the Fmoc group and acylation with IBut-OH. The product was characterized by HPLC ($t_R$ 15.3 min, Condition B) and MALDI-TOF-MS, calcd for $C_{78}H_{129}N_{15}O_{17}$, 1,548.0. Found: m/z 1,548.8 $[M+H]^+$, 1,570.8 $[M+Na]^+$, 1,586.8 $[M+K]^+$.

Example 27i

Lit-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by Lit-OH. The product was characterized by HPLC ($t_R$ 13.1 min, Condition H) and MALDI-TOF-MS, calcd for $C_{92}H_{150}N_{14}O_{17}$, 1,723.1. Found: m/z 1,724.6 $[M+H]^+$, 1,746.6 $[M+Na]^+$, 1,761.5 $[M+K]^+$.

Example, 27j

TFA-Lit-D-Val-Thr-Val-D-Val-D-Pro-Orn-D-allo-Ile-cyclo(D-allo-Thr-D-allo-Ile-D-Val-Phe-ZDhb-Val).

Obtained as a side product during the preparation (trifluoroacetylion during the cyclization step) of Example 27i. The product was characterized by HPLC ($t_R$ 17.1 min, Condition H) and MALDI-TOF-MS, calcd for $C_{94}H_{159}F_3N_{14}O_{18}$, 1,819.1. Found: m/z 1,820.6 $[M+H]^+$, 1,842.6 $[M+Na]^+$, 1,858.6 $[M+K]^+$.

Example 27k

Tico-D-Val-Thr-Val-D-Val-D-Pro-Orn-D-allo-Ile-cyclo(D-allo-Thr-D-allo-Ile-D-Val-Phe-ZDhb-Val).

Experimental procedures as decribed in Examples 1-7, starting with 200 mg of resin, were carried out with the only exceptions that, in Example 3, 5-MeHex was replaced by Tico-OH. The product was characterized by HPLC ($t_R$ 16.8 min, Condition H) and ES-MS, calcd for $C_{92}H_{158}N_{14}O_{16}$, 1,715.2. Found: m/z 858.2 $[M+H]+/2$, 1,171.8 $[M+H]^+$.

Example 28

H-D-Val-Thr-Val-D-Val-D-Pro-Orn-D-allo-Ile-cyclo(D-allo-Thr-D-allo-Ile-D-Val-Phe-ZDhb-Val).

Experimental procedures as described in Examples 1-7, starting with 200 mg of resin, were carried out with the only exceptions that, in Example 3, 5-MeHex was not incorporated. The product was characterized by HPLC ($t_R$ 11.6 mm, Condition B) and MALDI-TOF-MS, calcd for $C_{68}H_{112}N_{14}O_{15}$, 1,364.8. Found: m/z 1,388.3 [M+Na]$^+$, 1,404.3 [M+K]$^+$.

Example 28bis

H-D-Val-Thr-Val-D-Val-D-Pro-Orn-D-allo-Ile-cyclo(D-allo-Thr-D-allo-Ile-Val-Phe-Z-Dhb-Val).

Obtained as a side product during the preparation (racemization during the cyclization step) of Example 28. The product was characterized by HPLC ($t_R$ 12.9 min, Condition B) and MALDI-TOF-MS, calcd for $C_{68}H_{112}N_{14}O_{15}$, 1,364.8. Found: m/z 1,388.4 [M+Na]$^+$, 1,404.4 [M+K]$^+$.

Example 29

5-MeHex-D-Val-Thr-Val-D-Val-D-Pro-D-allo-Ile-cyclo(D-allo-Thr-D-allo-Ile-D-Val-Phe-ZDhb-Val).

Experimental procedures essentially as decribed in Examples 1-7, but according to the scheme 2.

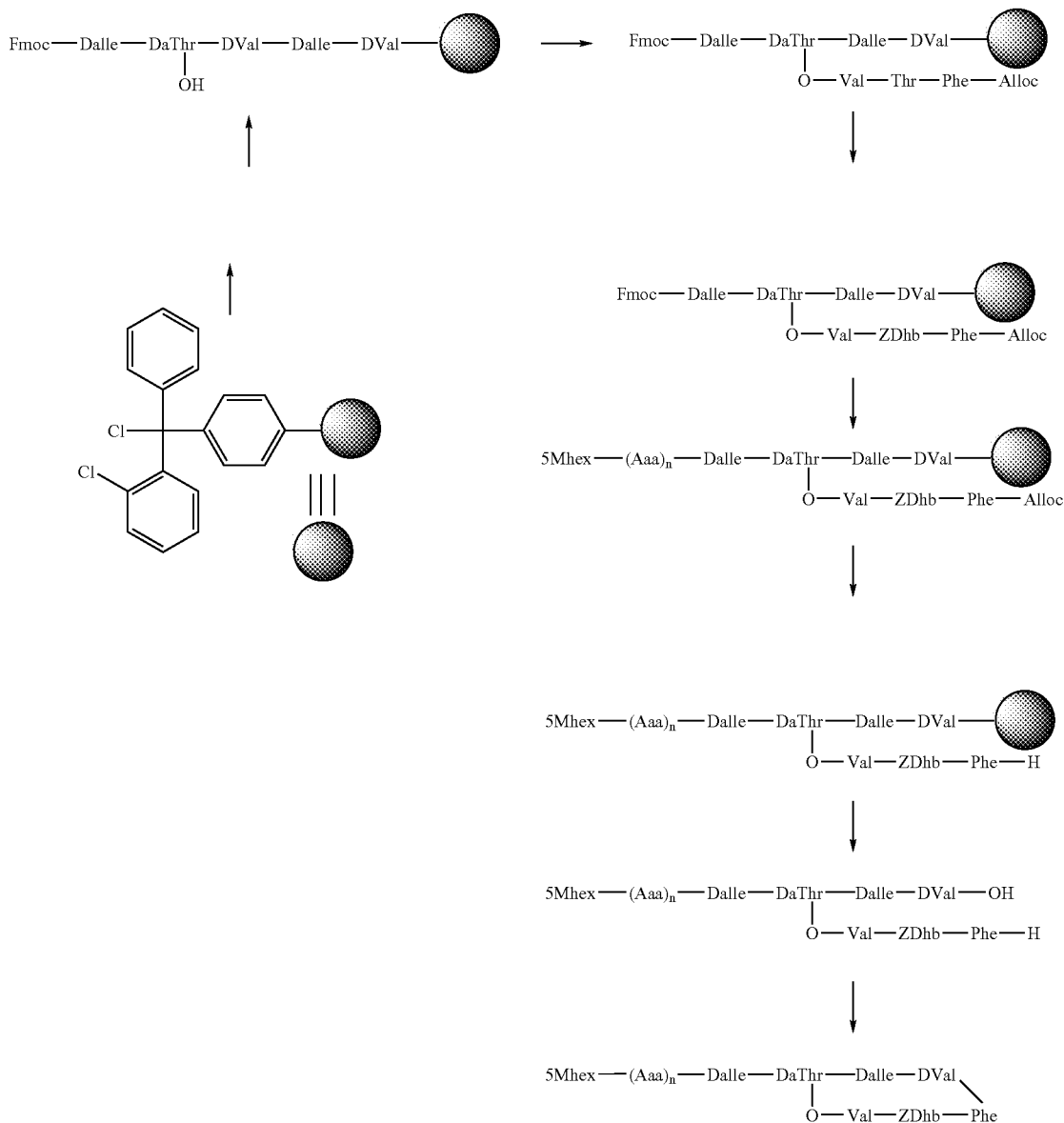

Scheme 2

The synthesis starts with 200 mg of resin and Fmoc-Orn (Boc)-OH was not incorporated. The product was characterized by HPLC ($t_R$ 23.9 min, Condition A) and MALDI-TOF-MS, calcd for $C_{70}H_{114}N_{12}O_{15}$, 1,362.9. Found: m/z 1,386.4 [M+Na]$^+$. 1,402.4 [M+K]$^+$.

Example 29bis

5-MeHex-D-Val-Thr-Val-D-Val-D-Pro-D-allo-Ile-cyclo(D-allo-Thr-D-allo-Ile-Val-Phe-Z-Dhb-Val).

Obtained as a side product during the preparation (racemization during the cyclization step) of Example 29. The product was characterized by HPLC and MALDI-TOF-MS.

Example 30

5-MeHex-D-Val-Thr-Val-D-Val-D-allo-Ile-cyclo(D-allo-Thr-D-allo-Ile-D-Val-Phe-Z-Dhb-Val).

Experimental procedures essentially as decribed in Examples 1-7, but according the scheme 2. The synthesis starts with 200 mg of resin and Fmoc-Orn(Boc)-OH and Fmoc-D-Pro-OH were not incorporated. The product was characterized by HPLC ($t_R$ 20.3 min, Condition B) and MALDI-TOF-MS, calcd for $C_{65}H_{107}N_{11}O_{14}$, 1,265.8. Found: m/z 1,288.5 [M+Na]$^+$, 1,304.5 [M+K]$^+$.

Example 31

5-MeHex-D-Val-Thr-Val-D-allo-Ile-cyclo(D-allo-Thr-D-allo-Ile-D-Val-Phe-Z-Dhb-Val).

Experimental procedures essentially as decribed in Examples 1-7, but according the scheme 2. The synthesis starts with 200 mg of resin and Fmoc-Orn(Boc)-OH, Fmoc-D-Pro-OH, and Fmoc-D-Val-OH were not incorporated. The product was characterized by HPLC ($t_R$ 20.0 min, Condition B) and MALDI-TOF-MS, calcd for $C_{60}H_{98}N_{10}O_{13}$, 1,166.7. Found: m/z 1,190.9 [M+Na]$^+$, 1,206.9 [M+K]$^+$.

Example 32

5-MeHex-D-Val-Thr-D-allo-Ile-cyclo(D-allo-Thr-D-allo-Ile-D-Val-Phe-ZDhb-Val).

Experimental procedures essentially as decribed in Examples 1-7, but according the scheme 2. The synthesis starts with 200 mg of resin and Fmoc-Orn(Boc)-OH, Fmoc-D-Pro-OH, Fmoc-D-Val-OH, and Fmoc-Val-OH were not incorporated. The product was characterized by HPLC ($t_R$ 24.6 min, Condition A) and MALDI-TOF-MS, calcd for $C_{55}H_{89}N_9O_{12}$, 1,067.7. Found: m/z 1,068.7 [M+H]$^+$, 1,090.6 [M+Na]$^+$, 1,106.5[M+K]$^+$.

Example 33

5-MeHex-D-Val-D-allo-Ile-cyclo(D-allo-Thr-D-allo-Ile-D-Val-Phe-ZDhb-Val).

Experimental procedures essentially as decribed in Examples 1-7, but according the scheme 2. The synthesis starts with 200 mg of resin and Fmoc-Orn(Boc)-OH, Fmoc-D-Pro-OH, Fmoc-D-Val-OH, Fmoc-Val-OH, and Fmoc-Thr(tBu)-OH were not incorporated. The product was characterized by HPLC ($t_R$ 19.8 min, Condition B) and MALDI-TOF-MS, calcd for $C_{51}H_{82}N_8O_{10}$, 966.6. Found: m/z 990.7 [M+Na]$^+$, 1007.2 [M+K]$^+$.

Example 34

5-MeHex-D-allo-Ile-cyclo(D-allo-Thr-D-allo-Ile-D-Val-Phe-ZDhb-Val).

Experimental procedures essentially as decribed in Examples 1-7, but according the scheme 2. The synthesis starts with 200 mg of resin and Fmoc-Orn(Boc)-OH, Fmoc-D-Pro-OH, Fmoc-D-Val-OH, Fmoc-Val-OH, Fmoc-Thr (tBu)-OH, and Fmoc-D-Val-OH were not incorporated. The product was characterized by HPLC ($t_R$ 22.0 min, Condition B) and MALDI-TOF-MS, calcd for $C_{46}H_{73}N_7O_9$, 867.6. Found: m/z 890.6 [M+Na]$^+$, 906.6 [M+K]$^+$.

Example 35

5-MeHex-cyclo(D-alloThr-D-allo-le-D-Val-Phe-ZDhb-Val)

Experimental procedures essentially as decribed in Examples 1-7, but according the scheme 2. The synthesis starts with 200 mg of resin and Fmoc-D-allo-Ile-OH, Fmoc-Orn(Boc)-OH, Fmoc-D-Pro-OH, Fmoc-D-Val-OH, Fmoc-Val-OH, Fmoc-Thr(tBu)-OH, and Fmoc-D-Val-OH were not incorporated. The product was characterized by HPLC ($t_R$ 17.1 min, Condition B) and ESMS, calcd for $C_{40}H_{62}N_6O_8$, 754.5 Found: m/z 755.7 [M+H]$^+$, 777.7 [M+Na]$^+$, 793.7 [M+K]$^+$.

Bioactivity

The bioactivity of compounds of this invention is demonstrated by the results in the following tables obtained in accordance with the methodology of Berjeron et al., Biochem and Bioph Res. Comm., 1984, 121, 3, 848-854. The cell lines are P388, murine lymphoma; A549, human lung carcinoma; HT-29, human colon carcinoma; MEL-28, human melanoma; DU-145, human prostate carcinoma.

TABLE

Kahalalide F congeners

| Compound | Cycle | Chain** | MW |
|---|---|---|---|
| 27j | cyclo(D-allo-Thr-D-allo-Ile-D-Val-Phe-Z-Dhb-Val) | Terminal: TFA-Lit- | 1820 |
| 27i | cyclo(D-allo-Thr-D-allo-Ile-D-Val-Phe-Z-Dhb-Val) | Terminal: lithocholoyl(Lit). | 1724 |
| 27 | cyclo(D-allo-Thr-D-allo-Ile-D-Val-Phe-Z-Dhb-Val) | Terminal: palmitoyl Palm | 1604 |
| 27 bis | cyclo(D-allo-Thr-D-allo-Ile-Val-Phe-Z-Dhb-Val) | Terminal: palmitoyl Palm | 1604 |
| 27g | cyclo(D-allo-Thr-D-allo-Ile-D-Val-Phe-Z-Dhb-Val) | Terminal: 4-(4-acetoxybutanoyloxy)-butyryl (AcButBut-) | 1579 |
| 27h | cyclo(D-allo-Thr-D-allo-Ile-D-Val-Phe-Z-Dhb-Val) | IBut-D-allo-Ile-D-Val-L-Thr-L-Val-D-Val-D-Pro-L-Orn-D-allo-Ile- | 1548 |
| 20e | cyclo(D-allo-Thr-D-allo-Ile-D-Val-Phe-D-Phe-Val)-D-Phe: a,b-didehydro-phenylalanine | 5-MeHex-D-Val-L-Thr-L-Val-D-Val-D-Pro-L-Orn-D-allo-Ile- | 1539 |
| 20c | cyclo(D-allo-Thr-D-allo-Ile-D-Val-Phe-Thr-Val) | 5-MeHex-D-Val-L-Thr-L-Val-D-Val-D-Pro-L-Orn-D-allo-Ile- | 1495 |
| 27c | cyclo(D-allo-Thr-D-allo-Ile-D-Val-Phe-Z-Dhb-Val) | Terminal: 4-acetoxibutyryl (4-AcBut) | 1493 |
| 20 | cyclo(D-allo-Thr-D-allo-Ile-D-Val-Phe-L-Etg-Val) | 5-MeHex-D-Val-L-Thr-L-Val-D-Val-D-Pro-L-Orn-D-allo-Ile- | 1479 |

TABLE-continued

Kahalalide F congeners

| Compound | Cycle | Chain** | MW |
|---|---|---|---|
| 20b | cyclo(D-allo-Thr-D-allo-Ile-D-Val-Phe-D-Etg-Val) | 5-MeHex-D-Val-L-Thr-L-Val-D-Val-D-Pro-L-Orn-D-allo-Ile- | 1479 |
| 27a | cyclo(D-allo-Thr-D-allo-Ile-D-Val-Phe-Z-Dhb-Val) | Terminal: N,N-dimethyl-4-aminobutyryl(4-DiMeABut) | 1478 |
| (as Scheuer) 15 | cyclo(D-allo-Thr-D-allo-Ile-D-Val-Phe-Z-Dhb-Val) | 5-MeHex-D-Val-L-Thr-D-Val-L-Val-D-Pro-L-Orn-D-allo-Ile- | 1477 |
| 15 bis | cyclo(D-allo-Thr-D-allo-Ile-Val-Phe-Z-Dhb-Val) | 5-MeHex-D-Val-L-Thr-D-Val-L-Val-D-Pro-L-Orn-D-allo-Ile- | 1477 |
| 26 | cyclo(D-allo-Thr-D-allo-Ile-D-Val-Phe-Z-Dhb-Val) | Terminal: Heptanoyl (Hep) | 1477 |
| 26 bis | cyclo(D-allo-Thr-D-allo-Ile-Val-Phe-Z-Dhb-Val) | Terminal: Heptanoyl (Hep) | 1477 |
| (Rinehart) 7 | cyclo(D-allo-Thr-D-allo-Ile-D-Val-Phe-Z-Dhb-Val) | 5-MeHex-D-Val-L-Thr-L-Val-D-Val-D-Pro-L-Orn-D-allo-Ile- | 1477 |
| 7 bis | cyclo(D-allo-Thr-D-allo-Ile-Val-Phe-Z-Dhb-Val) | 5-MeHex-D-Val-L-Thr-L-Val-D-Val-D-Pro-L-Orn-D-allo-Ile- | 1477 |
| 24 | cyclo(D-allo-Thr-D-allo-Ile-D-Val-Phe-Z-Dhb-Val) | Terminal: 3,3-dimethylbutyryl (3,3-DiMeBut) | 1463 |
| 24 bis | cyclo(D-allo-Thr-D-allo-Ile-Val-Phe-Z-Dhb-Val) | Terminal: 3,3-dimethylbutyryl (3,3-DiMeBut) | 1463 |
| 25 | cyclo(D-allo-Thr-D-allo-Ile-D-Val-Phe-Z-Dhb-Val) | Terminal: 3-Methylpentanoyl (4-MePen) | 1463 |
| 25 bis | cyclo(D-allo-Thr-D-allo-Ile-Val-Phe-Z-Dhb-Val) | Terminal: 3-Methylpentanoyl (4-MePen) | 1463 |
| 27f | cyclo(D-allo-Thr-D-allo-Ile-D-Val-Phe-Z-Dhb-Val) | Terminal: trifluoracetyl (TFA) | 1461 |
| 27b | cyclo(D-allo-Thr-D-allo-Ile-D-Val-Phe-Z-Dhb-Val) | Terminal: 2,4-hexadienoyl (Hedo) | 1459 |
| 27d | cyclo(D-allo-Thr-D-allo-Ile-D-Val-Phe-Z-Dhb-Val) | Terminal: 4-hydroxybutyryl | 1451 |
| 23 | cyclo(D-allo-Thr-D-allo-Ile-D-Val-Phe-Z-Dhb-Val) | Terminal: 3-Methylbutyryl (3-MetBut) | 1451 |
| 23b | cyclo(D-allo-Thr-D-allo-Ile-Val-Phe-Z-Dhb-Val) | Terminal: 3-Methylbutyryl (3-MetBut) | 1451 |
| 22 | cyclo(D-allo-Thr-D-allo-Ile-D-Val-Phe-Z-Dhb-Val) | Terminal: Butyryl (But) | 1435 |
| 22b | cyclo(D-allo-Thr-D-allo-Ile-Val-Phe-Z-Dhb-Val) | Terminal: Butyryl | 1435 |
| 27c | cyclo(D-allo-Thr-D-allo-Ile-D-Val-Phe-Z-Dhb-Val) | Terminal: acetyl | 1407 |
| 28 | cyclo(D-allo-Thr-D-allo-Ile-D-Val-Phe-Z-Dhb-Val) | Terminal: no fatty acid | 1365 |
| 28 bis | cyclo(D-allo-Thr-D-allo-Ile-Val-Phe-Z-Dhb-Val) | Terminal: no fatty acid | 1365 |
| 29 | cyclo(D-allo-Thr-D-allo-Ile-D-Val-Phe-Z-Dhb-Val) | 5-MeHex-D-Val-L-Thr-L-Val-D-Val-D-Pro-D-allo-Ile- | 1363 |
| 29 bis | cyclo(D-allo-Thr-D-allo-Ile-Val-Phe-Z-Dhb-Val) | 5-MeHex-D-Val-L-Thr-L-Val-D-Val-D-Pro-D-allo-Ile- | 1363 |
| 31 | cyclo(D-allo-Thr-D-allo-Ile-D-Val-Phe-Z-Dhb-Val) | 5-MeHex-D-Val-L-Thr-L-Val-D-allo-Ile- | 1167 |
| 32 | cyclo(D-allo-Thr-D-allo-Ile-D-Val-Phe-Z-Dhb-Val) | 5-MeHex-D-Val-L-Thr-D-allo-Ile- | 1068 |
| 19 | L-Phe-D-Leu-L-Pro-__-Thr-Gly-D-Ser | 5-MeHex-L-Tyr- | 878 |
| 34 | cyclo(D-allo-Thr-D-allo-Ile-D-Val-Phe-Z-Dhb-Val) | 5-MeHex-D-allo-Ile | 868 |
| 35 | cyclo(D-allo-Thr-D-allo-Ile-D-Val-Phe-Z-Dhb-Val) | 5-MeHex- | 754 |

**Compounds where the chain is indicated Terminal have the same chain as in compound 7, but with the indicated substitution for the 5-MeHex.

TABLE

Cytotoxicity of Kahalalide F congeners
IC50 (millimol) values for derivatives

| Compound | A549M | DU145M | HT29M | MEL28M | p388M |
|---|---|---|---|---|---|
| 27j | 5.49E−05 | 5.49E−05 | 5.49E−05 | 5.49E−05 | 2.75E−03 |
| 27i | 5.80E−04 | 5.80E−04 | 2.90E−05 | 1.45E−04 | 1.45E−03 |
| 27 | 1.56E−04 | 3.12E−05 | 6.23E−05 | 6.23E−05 | 3.12E−03 |
| 27 bis | >3.12E−03 | 1.56E−03 | 6.23E−05 | 6.23E−04 | >3.12E−03 |
| 27g | >6.33E−04 | >6.33E−04 | 1.58E−03 | 3.17E−03 | >3.17E−03 |
| 27h | NA | NA | NA | NA | NA |
| 20e | 3.25E−03 | 6.50E−04 | NA | NA | NA |
| 20c | NA | NA | NA | NA | NA |
| 27c | NA | NA | 6.70E−04 | 3.35E−03 | NA |
| 20 | >3.38E−03 | >3.38E−03 | >3.38E−03 | >3.38E−03 | >3.38E−03 |
| 20b | >3.38E−03 | 3.38E−03 | 3.38E−03 | >3.38E−03 | >3.38E−03 |
| 27a | NA | NA | NA | NA | NA |
| (as Scheuer) 15 | >3.39E−03 | 3.39E−03 | 3.39E−03 | >3.39E−03 | >3.39E−03 |
| 15 bis | >3.39E−03 | >3.39E−03 | >3.39E−03 | >3.39E−03 | >3.39E−03 |
| 26 | 3.39E−04 | 3.39E−05 | 6.77E−04 | 1.69E−03 | 3.39E−03 |
| 26 bis | >3.39E−03 | >3.39E−03 | 3.39E−04 | 1.69E−03 | >3.39E−03 |
| (Rinehart) 7 | 3.39E−04 | 1.69E−04 | 3.39E−05 | 3.39E−04 | >3.39E−03 |
| 7 bis | >3.39E−03 | >3.39E−03 | >3.39E−03 | >3.39E−03 | >3.39E−03 |
| 24 | 1.71E−03 | 3.42E−04 | 3.42E−04 | 3.42E−03 | >3.42E−03 |

TABLE-continued

Cytotoxicity of Kahalalide F congeners
IC50 (millimol) values for derivatives

| Compound | A549M | DU145M | HT29M | MEL28M | p388M |
|---|---|---|---|---|---|
| 24 bis | >3.42E−03 | >3.42E−03 | 3.42E−04 | >3.42E−03 | >3.42E−03 |
| 25 | 3.42E−04 | 3.42E−04 | >3.42E−03 | >3.42E−03 | >3.42E−03 |
| 25 bis | >3.42E−03 | >3.42E−03 | >3.42E−03 | >3.42E−03 | >3.42E−03 |
| 27f | NA | 3.42E−03 | >3.42E−03 | 3.42E−03 | 3.42E−03 |
| 27b | 3.43E−03 | 6.85E−04 | 3.43E−03 | NA | NA |
| 27d | NA | NA | NA | NA | NA |
| 23 | >3.45E−03 | >3.45E−04 | >3.45E−05 | >3.45E−04 | >3.45E−03 |
| 23b | >3.45E−03 | >3.45E−03 | >3.45E−03 | >3.45E−03 | >3.45E−03 |
| 22 | >3.48E−03 | 1.74E−03 | NA | NA | NA |
| 22b | >3.48E−03 | >3.48E−03 | 1.74E−03 | >3.48E−03 | >3.48E−03 |
| 27c | NA | >3.55E−03 | >3.55E−03 | >3.55E−03 | >3.55E−03 |
| 28 | >3.66E−03 | >3.66E−03 | >3.66E−03 | >3.66E−03 | >3.66E−03 |
| 28 bis | >3.66E−03 | >3.66E−03 | NA | NA | NA |
| 29 | >3.67E−03 | >3.67E−03 | >3.67E−03 | >3.67E−03 | >3.67E−03 |
| 29 bis | >3.67E−03 | >3.67E−03 | >3.67E−03 | >3.67E−03 | >3.67E−03 |
| 31 | >4.28E−04 | >4.28E−05 | >4.28E−03 | >4.28E−03 | >4.28E−03 |
| 32 | NA | NA | 4.68E−05 | 4.68E−05 | >4.68E−03 |
| 19 | >5.69E−03 | >5.69E−03 | NA | NA | NA |
| 34 | NA | NA | >5.76E−03 | >5.76E−03 | >5.76E−03 |
| 35 | >5.76E−03 | >5.76E−03 | >5.76E−03 | >5.76E−03 | >5.76E−03 |

REFERENCES

Hamann, M. T.; Scheuer, P. J. *J. Am. Chem. Soc.,* 1993. "Kahalalide F: a Bioactive Depsipeptide from the Sacoglossan Mollusk *Elysia refescens* and the Green *Alga Bryopsis* sp.", vol. 115, pp. 5825-5826.

Hamann, M. T., et al. *J. Org. Chem.,* 1996. "Kahalalides: Bioactive Peptides from Marine Mollusk *Elysia rufescens* and its Algal Diet *Bryopsis* sp.", vol. 61, pp. 6594-6660.

Garcia-Rocha, M., et al. *Cancer Lett.,* 1996. "The Antitumoral Compound Kahalalide F Acts on Cell Lysosomes", vol. 99, pp. 43-50.

Hamann, M. T., et al. *J. Org. Chem.,* 1998. "Kahalalides: Bioactive Peptides from Marine Mollusk *Elysia rufescens* and its Algal Diet *Bryopsis* sp.", vol. 63, p. 485 (Correction of *J. Org. Chem.,* 1996, vol. 61, pp. 6594-6660).

Lloyd-Williams, P., et al. *Chemical Approaches to the Synthesis of Peptides and Proteins*. CRC Press, Boca Raton (FL), 1997.

Goetz, G., et al. *J. Nat. Prod.,* 1997. "Two Acyclic Kahalalides from the Sacoglossan Mollusk *Elysia rufescens*", vol. 60, pp. 562-567.

Goetz, G., et al. *Tetrahedron,* 1999. The Absolute Stereochemistry of Kahalalide F", vol. 55, pp. 7739-7746.

Kan, Y., et al. J. Nat. Prod., 1999, vol. 62, pp. 1169-1172.

Horgen, F. D. et al. J. Nat. Prod., 2000, vol. 63, pp. 152-154.

The invention claimed is:

1. A compound selected from the group consisting of:
5-MeHex-D-Val-Thr-Val-D-Val-D-Pro-Orn-D-allo-Ile-cyclo(D-allo-Thr-D-allo-Ile-Val-Phe-Z-Dhb-Val);
5-MeHex-D-Val-Thr-Val-D-Val-D-Pro-Orn-D-allo-Ile-cyclo(D-allo-Thr-D-allo-Ile-Val-Phe-Z-Dhb-Val);
5-MeHex-D-Val-Thr-Val-D-Val-D-Pro-Orn-D-allo-Ile-cyclo(D-allo-Thr-D-allo-Ile-D-Val-Phe-Etg-Val);
5-MeHex-D-Val-Thr-Val-D-Val-D-Pro-Orn-D-allo-Ile-cyclo(D-allo-Thr-D-allo-Ile-D-Val-Phe-D-Etg-Val);
5-MeHex-D-Val-Thr-Val-D-Val-D-Pro-Orn-D-allo-Ile-cyclo(D-allo-Thr-D-allo-Ile-D-Val-Phe-D-Thr-Val);
5-MeHex-D-Val-Thr-Val-D-Val-D-Pro-Orn-D-allo-Ile-cyclo(D-allo-Thr-D-allo-Ile-D-Val-Phe-D-allo-Thr-Val);
5-MeHex-D-Val-Thr-Val-D-Val-D-Pro-Orn-D-allo-Ile-cyclo(D-allo-Thr-D-allo-Ile-D-Val-Phe-D-Phe-Val);
5-MeHex-D-Val-Thr-Val-D-Val-D-Pro-Orn-D-allo-Ile-cyclo(D-Dpa-D-allo-Ile-D-Val-Phe-Z-Dhb-Val);
But-D-Val-Thr-Val-D-Val-D-Pro-Orn-D-allo-Ile-cyclo (D-allo-Thr-D-allo-Ile-D-Val-Phe-Z-Dhb-Val);
But-D-Val-Thr-Val-D-Val-D-Pro-Orn-D-allo-Ile-cyclo (D-allo-Thr-D-allo-Ile-Val-Phe-Z-Dhb-Val);
3-MeBut-D-Val-Thr-Val-D-Val-D-Pro-Orn-D-allo-Ile-cyclo(D-allo-Thr-D-allo-Ile-D-Val-Phe-Z-Dhb-Val);
3-MeBut-D-Val-Thr-Val-D-Val-D-Pro-Orn-D-allo-Ile-cyclo(D-allo-Thr-D-allo-Ile-Val-Phe-Z-Dhb-Val);
3,3-DiMeBut-D-Val-Thr-Val-D-Val-D-Pro-Orn-D-allo-Ile-cyclo(D-allo-Thr-D-allo-Ile-D-Val-Phe-Z-Dhb-Val);
3,3-DiMeBut-D-Val-Thr-Val-D-Val-D-Pro-Orn-D-allo-Ile-cyclo(D-allo-Thr-D-allo-Ile-Val-Phe-Z-Dhb-Val);
4-MePen-D-Val-Thr-Val-D-Val-D-Pro-Orn-D-allo-Ile-cyclo(D-allo-Thr-D-allo-Ile-D-Val-Phe-Z-Dhb-Val);
4-MePen-D-Val-Thr-Val-D-Val-D-Pro-Orn-D-allo-Ile-cyclo(D-allo-Thr-D-allo-Ile-Val-Phe-Z-Dhb-Val);
Hep-D-Val-Thr-Val-D-Val-D-Pro-Orn-D-allo-Ile-cyclo (D-allo-Thr-D-allo-Ile-D-Val-Phe-Z-Dhb-Val);
Hep-D-Val-Thr-Val-D-Val-D-Pro-Orn-D-allo-Ile-cyclo (D-allo-Thr-D-allo-Ile-Val-Phe-Z-Dhb-Val);
Pal-D-Val-Thr-Val-D-Val-D-Pro-Orn-D-allo-Ile-cyclo(D-allo-Thr-D-allo-Ile-D-Val-Phe-Z-Dhb-Val);
Pal-D-Val-Thr-Val-D-Val-D-Pro-Orn-D-allo-Ile-cyclo(D-allo-Thr-D-allo-Ile-Val-Phe-Z-Dhb-Val);
4-DiMeABut-D-Val-Thr-Val-D-Val-D-Pro-Orn-D-allo-Ile-cyclo(D-allo-Thr-D-allo-Ile-D-Val-Phe-Z-Dhb-Val);
2-Hedo-D-Val-Thr-Val-D-Val-D-Pro-Orn-D-allo-Ile-cyclo(D-allo-Thr-D-allo-Ile-D-Val-Phe-Z-Dhb-Val);
4-AcBut-D-Val-Thr-Val-D-Val-D-Pro-Orn-D-allo-Ile-cyclo(D-allo-Thr-D-allo-Ile-D-Val-Phe-Z-Dhb-Val);
4-HOBut-D-Val-Thr-Val-D-Val-D-Pro-Orn-D-allo-Ile-cyclo(D-allo-Thr-D-allo-Ile-D-Val-Phe-Z-Dhb-Val);
Ac-D-Val-Thr-Val-D-Val-D-Pro-Orn-D-allo-Ile-cyclo(D-allo-Thr-D-allo-Ile-D-Val-Phe-Z-Dhb-Val);
TFA-D-Val-Thr-Val-D-Val-D-Pro-Orn-D-allo-Ile-cyclo (D-allo-Thr-D-allo-Ile-D-Val-Phe-Z-Dhb-Val);
AcButBut-D-Val-Thr-Val-D-Val-D-Pro-Orn-D-allo-Ile-cyclo(D-allo-Thr-D-allo-Ile-D-Val-Phe-Z-Dhb-Val);

Lit-D-Val-Thr-Val-D-Val-D-Pro-Orn-D-allo-Ile-cyclo(D-allo-Thr-D-allo-Ile-D-Val-Phe-Z-Dhb-Val);

TFA-Lit-D-Val-Thr-Val-D-Val-D-Pro-Orn-D-allo-Ile-cyclo(D-allo-Thr-D-allo-Ile-D-Val-Phe-Z-Dhb-Val);

Tico-D-Val-Thr-Val-D-Val-D-Pro-Orn-D-allo-Ile-cyclo(D-allo-Thr-D-allo-Ile-D-Val-Phe-Z-Dhb-Val);

H-D-Val-Thr-Val-D-Val-D-Pro-Orn-D-allo-Ile-cyclo(D-allo-Thr-D-allo-Ile-D-Val-Phe-Z-Dhb-Val);

H-D-Val-Thr-Val-D-Val-D-Pro-Orn-D-allo-Ile-cyclo(D-allo-Thr-D-allo-Ile-Val-Phe-Z-Dhb-Val);

5-MeHex-D-Val-Thr-Val-D-Val-D-Pro-D-allo-Ile-cyclo(D-allo-Thr-D-allo-Ile-D-Val-Phe-Z-Dhb-Val);

5-MeHex-D-Val-Thr-Val-D-Val-D-Pro-D-allo-Ile-cyclo(D-allo-Thr-D-allo-Ile-Val-Phe-Z-Dhb-Val);

5-MeHex-D-Val-Thr-Val-D-Val-D-allo-Ile-cyclo(D-allo-Thr-D-allo-Ile-D-Val-Phe-Z-Dhb-Val);

5-MeHex-D-Val-Thr-Val-D-allo-Ile-cyclo(D-allo-Thr-D-allo-Ile-D-Val-Phe-Z-Dhb-Val);

5-MeHex-D-Val-Thr-D-allo-Ile-cyclo(D-allo-Thr-D-allo-Ile-D-Val-Phe-Z-Dhb-Val);

5-MeHex-D-Val-D-allo-Ile-cyclo(D-allo-Thr-D-allo-Ile-D-Val-Phe-Z-Dhb-Val);

5-MeHex-D-allo-Ile-cyclo(D-allo-Thr-D-a/Io-Ile-D-Val-Phe-Z-Dhb-Val);

IBut-D-allo-Ile-D-Val-Thr-Val-D-Val-D-Pro-Orn-D-allo-Ile-cyclo(D-allo-Thr-D-allo-Ile-D-Val-Phe-Z-Dhb-Val); and 5-MeHex-cyclo(D-allo-Thr-D-allo-Ile-D-Val-Phe-Z-Dhb-Val).

2. A compound according to claim 1, wherein the compound is 5-MeHex-D-Val-Thr-Val-D-Val-D-Pro-Orn-D-allo-Ile-cyclo(D-allo-Thr-D-allo-Ile-Val-Phe-Z-Dhb-Val).

3. A compound according to claim 1, wherein the compound is 5-MeHex-D-Val-Thr-D-Val-Val-D-Pro-Orn-D-allo-Ile-cyclo(D-allo-Thr-D-allo-Ile-Val-Phe-Z-Dhb-Val).

4. A compound according to claim 1, where the compound is 5-MeHex-D-Val-Thr-Val-D-Val-D-Pro-Orn-D-allo-Ile-cyclo(D-allo-Thr-D-allo-Ile-D-Val-Phe-Etg-Val).

5. A compound according to claim 1, where the compound is 5-MeHex-D-Val-Thr-Val-D-Val-D-Pro-Orn-D-allo-Ile-cyclo(D-allo-Thr-D-allo-Ile-D-Val-Phe-D-Etg-Val).

6. A compound according to claim 1, wherein the compound is 5-MeHex-D-Val-Thr-Val-D-Val-D-Pro-Orn-D-allo-Ile-cyclo(D-allo-Thr-D-allo-Ile-D-Val-Phe-D-Thr-Val).

7. A compound according to claim 1, wherein the compound is 5-MeHex-D-Val-Thr-Val-D-Val-D-Pro-Orn-D-allo-Ile-cyclo(D-allo-Thr-D-allo-Ile-D-Val-Phe-D-allo-Thr-Val).

8. A compound according to claim 1, wherein the compound is 5-MeHex-D-Val-Thr-Val-D-Val-D-Pro-Orn-D-allo-Ile-cyclo(D-allo-Thr-D-allo-Ile-D-Val-Phe-D-Phe-Val).

9. A compound according to claim 1, wherein the compound is 5-MeHex-D-Val-Thr-Val-D-Val-D-Pro-Orn-D-allo-Ile-cyclo(D-Dpa-D-allo-Ile-D-Val-Phe-Z-Dhb-Val).

10. A compound according to claim 1, wherein the compound is But-D-Val-Thr-Val-D-Val-D-Pro-Orn-D-allo-Ile-cyclo(D-allo-Thr-D-allo-Ile-D-Val-Phe-Z-Dhb-Val).

11. A compound according to claim 1, wherein the compound is But-D-Val-Thr-Val-D-Val-D-Pro-Orn-D-allo-Ile-cyclo(D-allo-Thr-D-allo-Ile-Val-Phe-Z-Dhb-Val).

12. A compound according to claim 1, wherein the compound is 3-MeBut-D-Val-Thr-Val-D-Val-D-Pro-Orn-D-allo-Ile-cyclo(D-allo-Thr-D-allo-Ile-D-Val-Phe-Z-Dhb-Val).

13. A compound according to claim 1, wherein the compound is 3-MeBut-D-Val-Thr-Val-D-Val-D-Pro-Orn-D-allo-Ile-cyclo(D-allo-Thr-D-allo-Ile-Val-Phe-Z-Dhb-Val).

14. A compound according to claim 1, wherein the compound is 3,3-DiMeBut-D-Val-Thr-Val-D-Val-D-Pro-Orn-D-allo-Ile-cyclo(D-allo-Thr-D-allo-Ile-D-Val-Phe-Z-Dhb-Val).

15. A compound according to claim 1, wherein the compound is 3,3-DiMeBut-D-Val-Thr-Val-D-Val-D-Pro-Orn-D-allo-Ile-cyclo(D-allo-Thr-D-allo-Ile-Val-Phe-Z-Dhb-Val).

16. A compound according to claim 1, wherein the compound is 4-MePen-D-Val-Thr-Val-D-Val-D-Pro-Orn-D-allo-Ile-cyclo(D-allo-Thr-D-allo-Ile-D-Val-Phe-Z-Dhb-Val).

17. A compound according to claim 11, wherein the compound is 4-MePen-D-Val-Thr-Val-D-Val-D-Pro-Orn-D-allo-Ile-cyclo(D-allo-Thr-D-allo-Ile-Val-Phe-Z-Dhb-Val).

18. A compound according to claim 1, wherein the compound is Hep-D-Val-Thr-Val-D-Val-D-Pro-Orn-D-allo-Ile-cyclo(D-allo-Thr-D-allo-Ile-D-Val-Phe-Z-Dhb-Val).

19. A compound according to claim 1, wherein the compound is Hep-D-Val-Thr-Val-D-Val-D-Pro-Orn-D-allo-Ile-cyclo(D-allo-Thr-D-allo-Ile-Val-Phe-Z-Dhb-Val).

20. A compound according to claim 1, wherein the compound is Pal-D-Val-Thr-Val-D-Val-D-Pro-Orn-D-allo-Ile-cyclo(D-allo-Thr-D-allo-Ile-D-Val-Phe-Z-Dhb-Val).

21. A compound according to claim 1, wherein the compound is Pal-D-Val-Thr-Val-D-Val-D-Pro-Orn-D-allo-Ile-cyclo(D-allo-Thr-D-allo-Ile-Val-Phe-Z-Dhb-Val).

22. A compound according to claim 1, wherein the compound is 4-DiMeABut-D-Val-Thr-Val-D-Val-D-Pro-Orn-D-allo-Ile-cyclo(D-allo-Thr-D-allo-Ile-D-Val-Phe-Z-Dhb-Val).

23. A compound according to claim 1, wherein the compound is 2-Hedo-D-Val-Thr-Val-D-Val-D-Pro-Orn-D-allo-Ile-cyclo(D-allo-Thr-D-allo-Ile-D-Val-Phe-Z-Dhb-Val).

24. A compound according to claim 1, wherein the compound is 4-AcBut-D-Val-Thr-Val-D-Val-D-Pro-Orn-D-allo-Ile-cyclo(D-allo-Thr-D-allo-Ile-D-Val-Phe-Z-Dhb-Val).

25. A compound according to claim 1, wherein the compound is 4-HOBut-D-Val-Thr-Val-D-Val-D-Pro-Orn-D-allo-Ile-cyclo(D-allo-Thr-D-allo-Ile-D-Val-Phe-Z-Dhb-Val).

26. A compound according to claim 1, wherein the compound is Ac-D-Val-Thr-Val-D-Val-D-Pro-Orn-D-allo-Ile-cyclo(D-allo-Thr-D-allo-Ile-D-Val-Phe-Z-Dhb-Val).

27. A compound according to claim 1, wherein the compound is TFA-D-Val-Thr-Val-D-Val-D-Pro-Orn-D-allo-Ile-cyclo(D-allo-Thr-D-allo-Ile-D-Val-Phe-Z-Dhb-Val).

28. A compound according to claim 1, wherein the compound is AcButBut-D-Val-Thr-Val-D-Val-D-Pro-Orn-D-allo-Ile-cyclo(D-allo-Thr-D-allo-Ile-D-Val-Phe-Z-Dhb-Val).

29. A compound according to claim 11, wherein the compound is Lit-D-Val-Thr-Val-D-Val-D-Pro-Orn-D-allo-Ile-cyclo(D-allo-Thr-D-allo-Ile-D-Val-Phe-Z-Dhb-Val).

30. A compound according to claim 1, wherein the compound is TFA-Lit-D-Val-Thr-Val-D-Val-D-Pro-Orn-D-allo-Ile-cyclo(D-allo-Thr-D-allo-Ile-D-Val-Phe-Z-Dhb-Val).

31. A compound according to claim 1, wherein the compound is Tico-D-Val-Thr-Val-D-Val-D-Pro-Orn-D-allo-Ile-cyclo(D-allo-Thr-D-allo-Ile-D-Val-Phe-Z-Dhb-Val).

32. A compound according to claim 1, wherein the compound is H-D-Val-Thr-Val-D-Val-D-Pro-Orn-D-allo-Ile-cyclo(D-allo-Thr-D-allo-Ile-D-Val-Phe-Z-Dhb-Val).

33. A compound according to claim 1, wherein the compound is H-D-Val-Thr-Val-D-Val-D-Pro-Orn-D-allo-Ile-cyclo(D-allo-Thr-D-allo-Ile-Val-Phe-Z-Dhb-Val).

34. A compound according to claim 1, wherein the compound is 5-MeHex-D-Val-Thr-Val-D-Val-D-Pro-D-allo-Ile-cyclo(D-allo-Thr-D-allo-Ile-D-Val-Phe-Z-Dhb-Val).

35. A compound according to claim 11, wherein the compound is 5-MeHex-D-Val-Thr-Val-D-Val-D-Pro-D-allo-Ile-cyclo(D-allo-Thr-D-allo-Ile-Val-Phe-Z-Dhb-Val).

36. A compound according to claim 11, wherein the compound is 5-MeHex-D-Val-Thr-Val-D-Val-D-allo-Ile-cyclo(D-allo-Thr-D-allo-Ile-D-Val-Phe-Z-Dhb-Val).

37. A compound according to claim 11, wherein the compound is 5-MeHex-D-Val-Thr-Val-D-allo-Ile-cyclo(D-allo-Thr-D-allo-Ile-D-Val-Phe-Z-Dhb-Val).

38. A compound according to claim 1, wherein the compound is 5-MeHex-D-Val-Thr-D-allo-Ile-cyclo(D-allo-Thr-D-allo-Ile-D-Val-Phe-Z-Dhb-Val).

39. A compound according to claim 1, wherein the compound is 5-MeHex-D-Val-D-allo-Ile-cyclo(D-allo-Thr-D-allo-Ile-D-Val-Phe-Z-Dhb-Val).

40. A compound according to claim 1, wherein the compound is 5-MeHex-D-allo-Ile-cyclo(D-allo-Thr-D-allo-Ile-D-Val-Phe-Z-Dhb-Val).

41. A compound according to claim 1, wherein the compound is IBut-D-allo-Ile-D-Val-Thr-Val-D-Val-D-Pro-Orn-D-allo-Ile-cyclo(D-allo-Thr-D-allo-Ile-D-Val-Phe-Z-Dhb-Val).

42. A compound according to claim 1, wherein the compound is 5-MeHex-cyclo(D-allo-Thr-D-allo-Ile-D-Val-Phe-Z-Dhb-Val).

43. A composition comprising a compound according to claim 1 and a pharmaceutically acceptable carrier or diluent.

44. A method of synthesizing a compound according to claim 1, wherein said compound comprises a cyclic portion, said method comprising a step of forming an amide bond between a carboxylic group of a (D or L) Val moiety and an amino group of a Phe moiety to accomplish a ring closure and form the cyclic portion of the compound according to claim 11, and wherein the starting material and product are optionally protected by one or more protecting groups, and wherein the carboxylic group participating in the amide bond formation and/or the amino group participating in the amide bond formation may optionally be protected or activated.

45. A method of treating cancer comprising administering a therapeutically-effective amount of a compound according to claim 1, wherein said cancer is selected from the group consisting of lung cancer, colon cancer, prostate cancer, lymphoma, and melanoma.

46. A compound having the following Formula II:

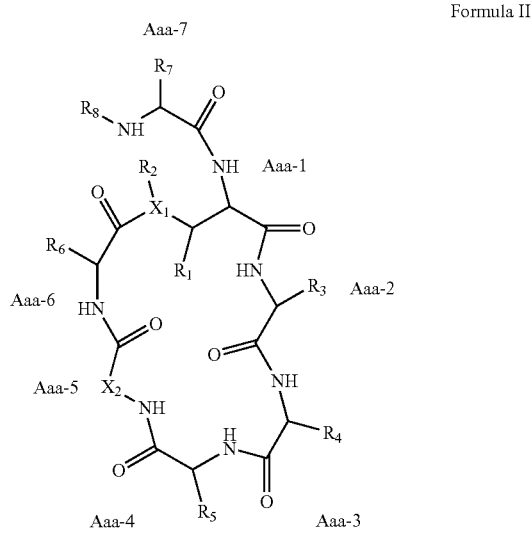

Formula II wherein $R_1$, $R_2$, $R_3$, $R_4$, $R_5$, $R_6$, $X_1$, and $X_2$ are each independently selected such that Aaa-1 is D-allo-Thr, Aaa-2 is D-allo-Ile, Aaa-3 is D-Val, Aaa-4 is Phe, Aaa-5 is Z-Dhb, and Aaa-6 is Val;

wherein $R_7$ is independently selected from the group consisting of H, or an alkyl, aryl, or aralkyl group optionally substituted with a hydroxy group, a mercapto group, an amino group, a guanidino group, or a halogen group;

wherein $R_7$ can optionally replace the hydrogen on the α-nitrogen to form a proline ring;

wherein $R_8$ is selected from formula III, IV, or V:

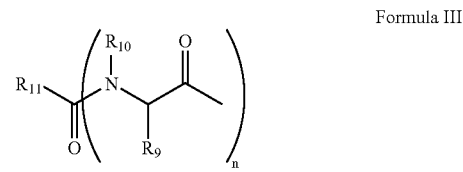

Formula III

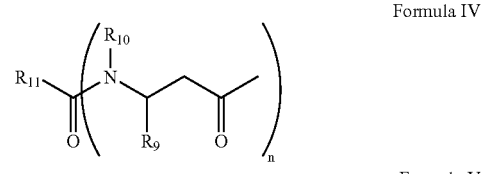

Formula IV

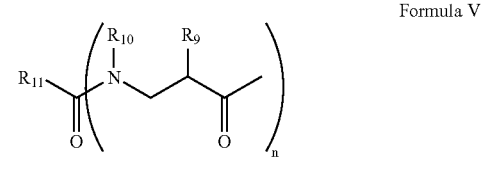

Formula V wherein $R_9$, $R_{10}$, and $R_{11}$ are each independently H or an alkyl, aryl, or aralkyl group optionally substituted with a hydroxy group, a mercapto group, an amino group, a guanidino group, a carboxyl group, a carboxamido group, or a halogen group;

wherein $R_9$ and $R_{10}$ can optionally form a ring;

wherein n is 0 to 6;

wherein repeating units in Formulas III, IV, and V may optionally be intermixed;

and wherein said compound of Formula II is not 5-MeHex-D-Val-Thr-D-Val-Val-D-Pro-Orn-D-allo-Ile-cyclo(D-allo-Thr-D-allo-Ile-D-Val-Phe-Z-Dhb-Val) or 5-Me-Hex-D-Val-Thr-Val-D-Val-D-Pro-Orn-D-allo-Ile-cyclo(D-allo-Thr-D-allo-Ile-D-Val-Phe-Z-Dhb-Val).

47. A composition comprising a compound according to claim 46 and a pharmaceutically acceptable carrier or diluent.

48. A method of synthesizing a compound according to claim 46, comprising a ring closure according to the following scheme:

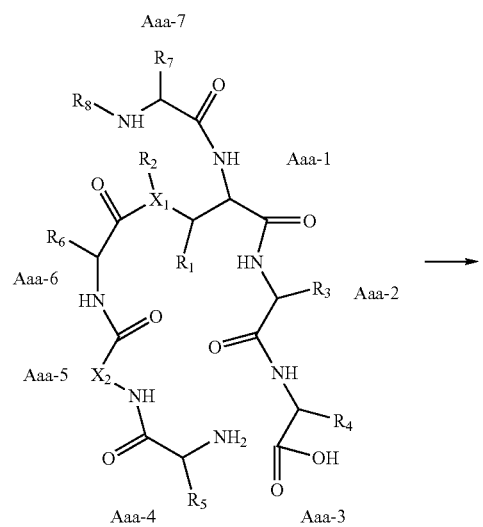

-continued

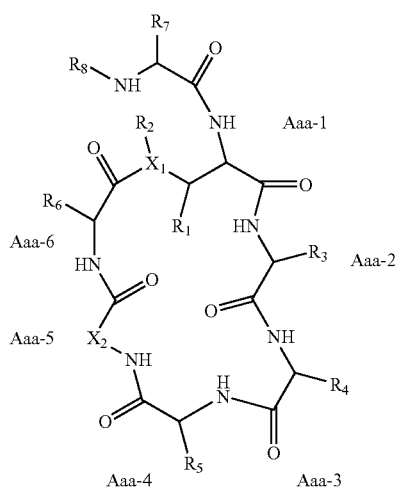

Formula II wherein the variables are defined according to claim 46, wherein the starting material and product are optionally protected by one or more protecting groups, and wherein the carboxylic group of $Aaa^3$ and/or the amino group of $Aaa^4$ of the staffing material may optionally be protected or activated.

49. A method of treating cancer comprising administering a therapeutically-effective amount of a compound according to claim 46, wherein said cancer is selected from the group consisting of lung cancer, colon cancer, prostate cancer, lymphoma, and melanoma.

* * * * *

UNITED STATES PATENT AND TRADEMARK OFFICE
CERTIFICATE OF CORRECTION

PATENT NO. : 7,482,429 B2  Page 1 of 1
APPLICATION NO. : 10/182881
DATED : January 27, 2009
INVENTOR(S) : Fernando Albericio et al.

It is certified that error appears in the above-identified patent and that said Letters Patent is hereby corrected as shown below:

Column 12, lines 19-20, please amend "a amino acid" to --α amino acid--;

Column 14, line 34, please amend "arylalkylaxyl" to --arylalkylaryl--;

Column 26, line 66, please amend "$C_{17}H_2ON_2O_5$" to --$C_{17}H_{20}N_2O_5$--;

Column 31, end of line 61, please amend "D-allolle-yclo" to --D-allo-lle-cyclo--;

Column 33, line 64, please amend "β-allo-Thr" to --D-allo-Thr--;

Column 45, Claim 1, line 22, please amend
"5-MeHex-D-allo-lle-cyclo(D-allo-Thr-D-a/lo-lle-D-Val-Phe-Z-Dhb-Val)" to
--5-MeHex-D-allo-lle-cyclo(D-allo-Thr-D-allo-lle-D-Val-Phe-Z-Dhb-Val)--;

Column 47, Claim 44, lines 23 to 24, please amend "cyclic portion of the compound according to claim 11" to --cyclic portion of the compound according to claim 1--.

Signed and Sealed this

Twenty-third Day of June, 2009

JOHN DOLL
*Acting Director of the United States Patent and Trademark Office*